United States Patent [19]

Jost et al.

[11] Patent Number: 5,888,773
[45] Date of Patent: Mar. 30, 1999

[54] METHOD OF PRODUCING SINGLE-CHAIN FV MOLECULES

[75] Inventors: Carolina R. Jost, Washington, D.C.; David M. Segal, Rockville, Md.; James S. Huston, Chestnut Hill, Mass.

[73] Assignee: The United States of America as represented by the Department of Health and Human Services, Washington, D.C.

[21] Appl. No.: 292,124

[22] Filed: Aug. 17, 1994

[51] Int. Cl.⁶ .......................... A61K 39/395; C07H 21/04
[52] U.S. Cl. ................... 435/69.6; 435/172.3; 435/328; 435/320.1; 530/387.3; 424/133.1
[58] Field of Search .................................. 435/69.6, 328, 435/320.1, 172.3; 530/387.3; 536/23.53; 424/133.1

[56] References Cited

FOREIGN PATENT DOCUMENTS

WO 94/15642  7/1994  WIPO.
WO 95/15769  6/1995  WIPO.

OTHER PUBLICATIONS

Delente, J. J., Trends in Biotechnology vol. 3, No. 9.
Nicholls, P.J. et al., "An Improved Method for Generating Single–Chain Antibodies from Hybridomas," *J. of Immuno. Methods*, 165(27):81–91 (1993).
George, A.J.T. et al., "Redirection of T Cell–Mediated Cytotoxicity by a Recombinant Single–Chain Fv Molecule," *J. Immunology*, 152(4):1802–1811 (1994).
Hand, P.H. et al., "Potential for Recombinant Immunoglobulin Constructs in the Management of Carcinoma," *Cancer*, 73(3):1105–1113 (1994).
Jost, C.R. et al., "Mammalian Expression and Secretion of Functional Single–Chain Fv Molecules," *J. Biol. Chem.*, 269(42) : 26267–26273 (1994).
Better, M. and Horwitz, A.H., "Expression of Engineered Antibodies and Antibody Fragments in Microorganisms," *Methods in Enzymology*, 178:476–496 (1989).
Biocca, S. et al., "Intracellular Expression of Anti–p21$^{ras}$ single Chain Fv Fragments Inhibits Meiotic Maturation of Xenopus Oocytes," *Biochem. and Biophy. Res. Cumm.*, 197(2):422–427 (1993).
Davis, S.J. et al., "High Level Expression in Chinese Hamster Ovary Cells of Soluble Forms of CD4 T Lymphocyte Glycoprotein Including Glycosylation Variants," *J. Bio. Chem.*, 265(18):10410–10418 (1990).
Eshhar, Z. et al., "Specific Activation and Targeting of Cytotoxic Lymphocytes Through Chimeric Single Chains Consisting of Antibody–Binding Domains and the $\gamma$ or $\zeta$ Subunits of the Immunoglobulin and T–Cell Receptors," *Proc. Natl. Acad. Sci. USA*, 90:720–724 (1993).
Glockshuber, R. et al., "A Comparison of Strategies to Stabilize Immunoglobulin Fv–Fragments", *Biochemistry*, 29:1362–1367 (1990).
Hayano, T. et al., "Two Distinct forms of Peptidylprolyl–cis–trans–isomerase Are Expressed Separately in Periplasmic and Cytoplasmic Compartments in Escherichia coli Cells," *Biochemistry*, 30:3041–3048 (1991).
Hedrick. S.M. et al., "Sequence Relationships Between Putative T–Cell Receptor Polypeptides and Immunoglobulins," *Nature*, 308:153–158 (1984).

(List continued on next page.)

*Primary Examiner*—Sheela Huff
*Assistant Examiner*—Julie E. Reeves
*Attorney, Agent, or Firm*—Townsend and Townsend and Crew LLP

[57] ABSTRACT

The invention relates to a method of producing single-chain Fv molecules in eukaryotic cells, and to secretable sFv proteins having at least one non-naturally occurring glycosylation site. The single-chain Fv molecules produced by this method are biologically active and capable of being secreted from eukaryotic cells into the cell culture medium.

14 Claims, 12 Drawing Sheets

OTHER PUBLICATIONS

Hochstenbach, F. et al., "Endoplasmic Reticulum Resident Protein of 90 Kilodaltons Associates with the T–and B–Cell Antigen Receptors and Major Histocompatibility Complex Antigens during Their Assembly," *Proc. Natl. Acad. Sci. USA*,89:4737–4738 (1992).

Hurtley, S.M. and Helenius, A., "Protein Oligomerization in the Endoplasmic Reticulum," *Annu. Rev. Cell. Biol.*5:277–307 (1989).

Huston, J.S. et al., "Protein Engineering of Antibody of Antibody Binding Sites: Recovery of Specific Activity in an Anti–Digoxin Single–Chain Fv Analogue Produced in *Escherichia coli*," *Proc. Natl. Acad. Sci. USA*, 85:5879–5883 (1988).

Huston, J.S. et al., "Medical Applications of Single–Chain Antibodies," *Intern. Rev. Immunol.*, 10:195–217 (1993).

Hwe, P. et al., "Lysis of Ovarian Cancer Cells by Human Lymphocytes Redirected with a Chimeric Gene Composed of an Antibody Variable Region and the Fc Receptor γ Chain," *J. of Exper. Medicine*, 178:361–366 (1993).

Johnson, S. and Bird, R.E., "Construction of Single–Chain Fv Derivatives of Monoclonal Antibodies and their Production in *Escherichia coli*," *Methods in Enzymology*, 203:88–98 (1991).

Kearse, K.P. and Singer A., "Isolation of Immature and Mature T Cell Receptor Complexes by Lectin Affinity Chromatography," *J. of Immunol. Methods*, 167:75–81 (1994).

Knittler, M.R. and Haas, I.G., "Interaction of BiP with Newly Synthesized Immunoglobulin Light Chain Molecules: Cycles of Sequential Binding and Release," *EMBO J.*, 11(4):1573–1581 (1992).

Kurucz, I. et al., "A Bacterially Expressed Single–Chain Fv Construct from the 2B4 T–Cell Receptor," *Proc. Natl. Acad. Sci. USA*, 90:3830–3834 (1993).

Marasco, W.A. et al., "Design Intercellular Expression, and Activity of a Human Anti–Human Immunodeficiency Virus Type 1 gp120 Single–Chain Antibody," *Proc. Natl. Acad. Sci. USA*, 90:7889–7893 (1993).

Jost, C.R. et al., "Mammalian Expression and Secretion of Functional Single–Chain Fv Molecules," *IBM Antibody Conference*, San Diego, Dec. 8–12 (1993).

Melnick, J. et al., "The Endoplasmic Reticulum Stress Protein GRP94, in Addition to BiP, Associates With Unassembled Immunoglobulin Chains," *J. Biol. Chem.*, 267(30):21303–21306 (1992).

Nicholls, J. et al., "An Improved Method for Generating Single–Chain Antibodies from Hybridomas," *J. Immunol. Methods*, 165:81–91 (1993).

Novotny, J. et al., "A Soluble, Single–Chain T–Cell Receptor Fragment Endowed with Antigen–Combining Properties," *Proc. Natl. Acad. Sci. USA*, 88:8646–8650 (1991).

Olden, K. et al., "Carbohydrate Moieties of Glycoproteins, A Re–evaluation of Their Function," *Biochimica et Biophysica Acta*, 650:209–232 (1982).

Pollok, B.A. et al., "Molecular Basis of the Cell–Surface Expression of Immunoglobulin μ Chain Without Light Chain in Human B Lymphocytes," *Proc. Natl. Acad. Sci. USA*, 84:9199–9203 (1987).

Pelham, H.R.B., "Control of Protein Exit From the Endoplasmic Reticulum," *Annu. Rev. Cell. Biol.*, 5:1–23 (1989).

Rothman, J.E. and Lodish, H.F., "Synchronised Transmembrane Insertion and Glycosylation of a Nascent Membrane Protein," *Nature*, 269:775–780 (1977).

Shu, L. et al., "Secretion of a Single–Gene–Encoded Immunoglobulin From Myeloma Cells," *Proc. Natl. Acad. Sci. USA*, 90:7995–7999 (1993).

Soo Hoo, W. F. et al., "Characterization of a Single–Chain T–Cell Receptor Expressed in *Escherichia coli*," *Proc. Natl. Acad. Sci. USA* , 89:4759–4763 (1992).

Stancovski, I. et al., "Targeting of T Lymphocytes to Neu/HER2–Expressing Cells Using Chimeric Single Chain Fv Receptors," *J. Immunol.*, 151(11):6577–6582 (1993).

Tarentino, A.L. et al., "The Release of Intact Oligosaccharides From Specific Glycoproteins by Endo–β–N–acetylglucosaminidase H," *J. Biol. Chem.*, 249(3):818–824 (1974).

Traunecker, A. et al., "Bispecific Single–Chain Molecules (Janusins) Target Cytotoxic Lymphocytes on HIV Infected Cells," *EMBO J.*, 10(12):3655–3659 (1991).

Ward, S.E., "Secretion of T Cell Receptor Fragments from Recombinant *Escherichia coli* Cells," *J. Mol. Biol.*, 244:885–890 (1992).

Wen, D. et al., "Expression of Genes Encoding Vesicular Stomatitis and Sindbis Virus Glycoproteins in Yeast Leads to Formation of Disulfide–Linked Oligomers," *Virology*, 153:150–154 (1986).

Wright A. and Morrison, S.L., "Antibody Variable Region Glycosylatin: Biochemical and Clinical Effects," *Spring Seminars Immunopathol*, 15:259–273 (1993).

Co., M.S. et al., "Genetically Engineered Deglycosylation of the Variable Domain Increases the Affinity of an Anti–CD33 Monoclonal Antibody," *Molecular Immunol.*, 30(15):1361–1367 (1993).

Holland, I.B. et al., "Secretion of Heterologous Proteins in *Escherichia coli*," *Methods in Enzymology*, 182:132–143 (1990).

Doral, H. et al., "Mammalian Cell Expression of Single–Chain Fv (sFv) Antibody Proteins and Their C–Terminal Fusions with Interleukin–2 and Other Effector Domains," *Bio/Technology*, 12:890–897 (1994).

```
CAG GTC CAA CTG CAG CAG TCT GGA CCT GAG CTG GAG AAG CCT GGC GCT
Gln Val Gln Leu Gln Gln Ser Gly Pro Glu Leu Glu Lys Pro Gly Ala
 1           5                  10                  15

TCA GTG AAG ATA TCC TGC AAG GCT TCT GGT TAC TCA TTC ACT GGC TAC
Ser Val Lys Ile Ser Cys Lys Ala Ser Gly Tyr Ser Phe Thr Gly Tyr
             20                  25                  30

ATC ATG AAC TGG GTA AAA CAG AAC AAT GGA AAG AGC CTT GAG TGG ATT
Ile Met Asn Trp Val Lys Gln Asn Asn Gly Lys Ser Leu Glu Trp Ile
         35                  40                  45

GGA AAT ATT GCT CCT TAC TAT GGT GGT ACT AGC TAC AAC CAG AAG TTC
Gly Asn Ile Ala Pro Tyr Tyr Gly Gly Thr Ser Tyr Asn Gln Lys Phe
     50                  55                  60

AAG GGC AAG GCC ACA TTG ACT GTA GAC AAA TCC TCC AGC ACA GCC TAC
Lys Gly Lys Ala Thr Leu Thr Val Asp Lys Ser Ser Ser Thr Ala Tyr
 65                  70                  75                  80

ATG CAG CTA AGC AGC CTG ACA TCT GAG GAC TCT GCA GTC TAT TTC TGT
Met Gln Leu Ser Ser Leu Thr Ser Glu Asp Ser Ala Val Tyr Phe Cys
             85                  90                  95

GCA AGA TGG GGA GGT ACT ATG ATT ACG GGT CTT GAC TAC TGG GGC CAA
Ala Arg Trp Gly Gly Thr Met Ile Thr Gly Leu Asp Tyr Trp Gly Gln
         100                 105                 110

GGC ACC ACT CTC ACA GTC TCC TCA
Gly Thr Thr Leu Thr Val Ser Ser
         115                 120
```

Figure 2A

```
GAT ATT GTC ATG ACC CAG TCT CCA GCA ATC ATG TCT GCA TCT CCA GGG
Asp Ile Val Met Thr Gln Ser Pro Ala Ile Met Ser Ala Ser Pro Gly
 1               5                  10                  15

GAA AAG GTC ACC ATG ACC TGC AGG GCC AGC TCA AGT GTA AGT TCC ACT
Glu Lys Val Thr Met Thr Cys Arg Ala Ser Ser Ser Val Ser Ser Thr
                 20                  25                  30

TAC TTC CAC TGG TAC CAG CAG AAG TCA GGT GCC TCC CCC AAA CTC TGG
Tyr Phe His Trp Tyr Gln Gln Lys Ser Gly Ala Ser Pro Lys Leu Trp
             35                  40                  45

ATT TAT AGC ACA TCC ACC TTG GCT TCT GGA GTC CCT GCT CGC TTC AGT
 Ile Tyr Ser Thr Ser Thr Leu Ala Ser Gly Val Pro Ala Arg Phe Ser
     50                  55                  60

GGC AGT GGG TCT GGG ACC TCT TAC TCT CTC ACA ATC AGC AGT GTG GAG
Gly Ser Gly Ser Gly Thr Ser Tyr Ser Leu Thr Ile Ser Ser Val Glu
 65                  70                  75                  80

GCT GAA GAT GCT GCC ACT TAT TAC TGC CAG CAG TAC AGT GGT TAC CCG
Ala Glu Asp Ala Ala Thr Tyr Tyr Cys Gln Gln Tyr Ser Gly Tyr Pro
                 85                  90                  95

CTC ACG TTC GGT GCT GGG ACC AAG CTG GAG CTG AAA CGC
Leu Thr Phe Gly Ala Gly Thr Lys Leu Glu Leu Lys Arg
                100                 105
```

Figure 2B

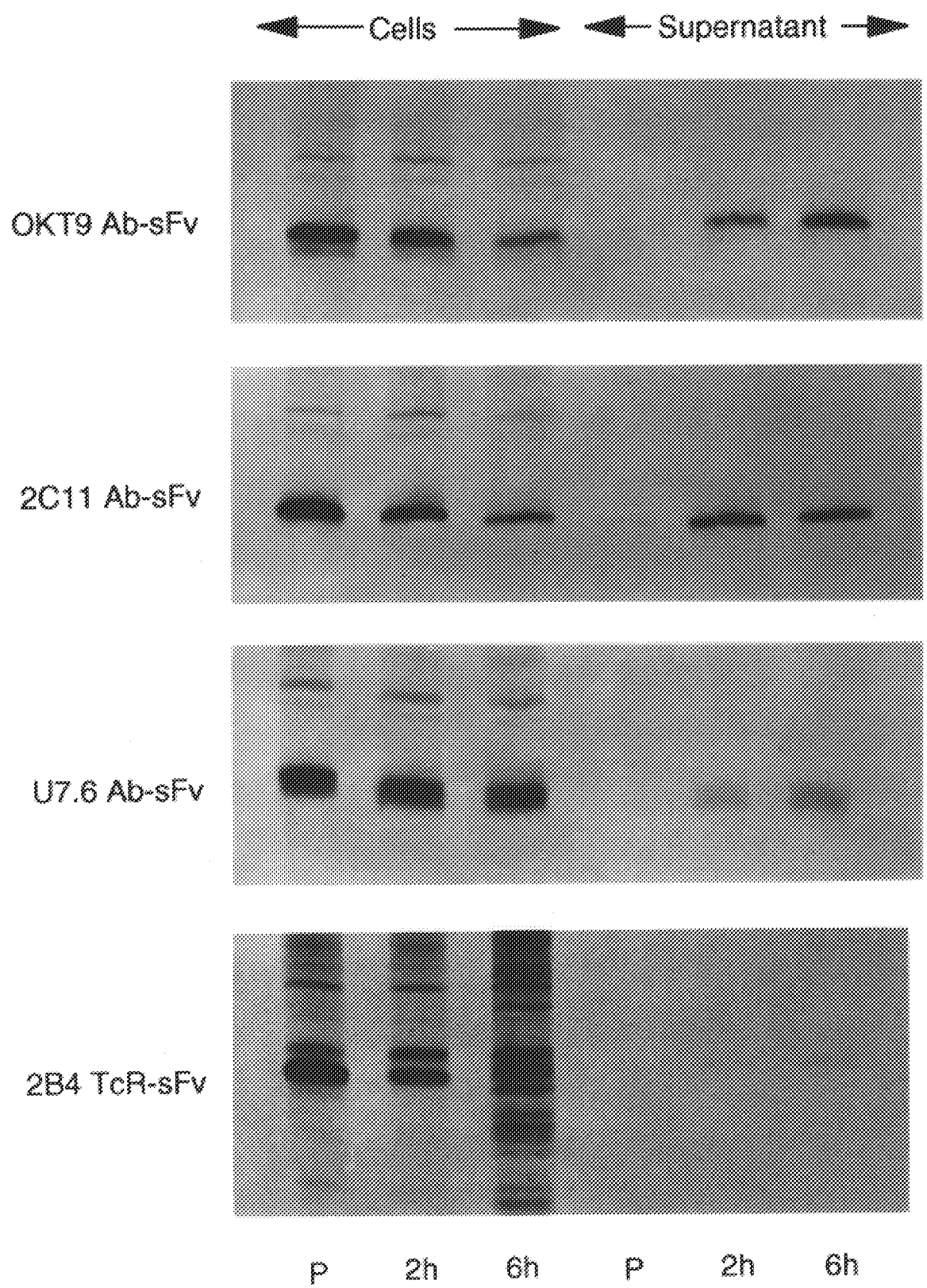

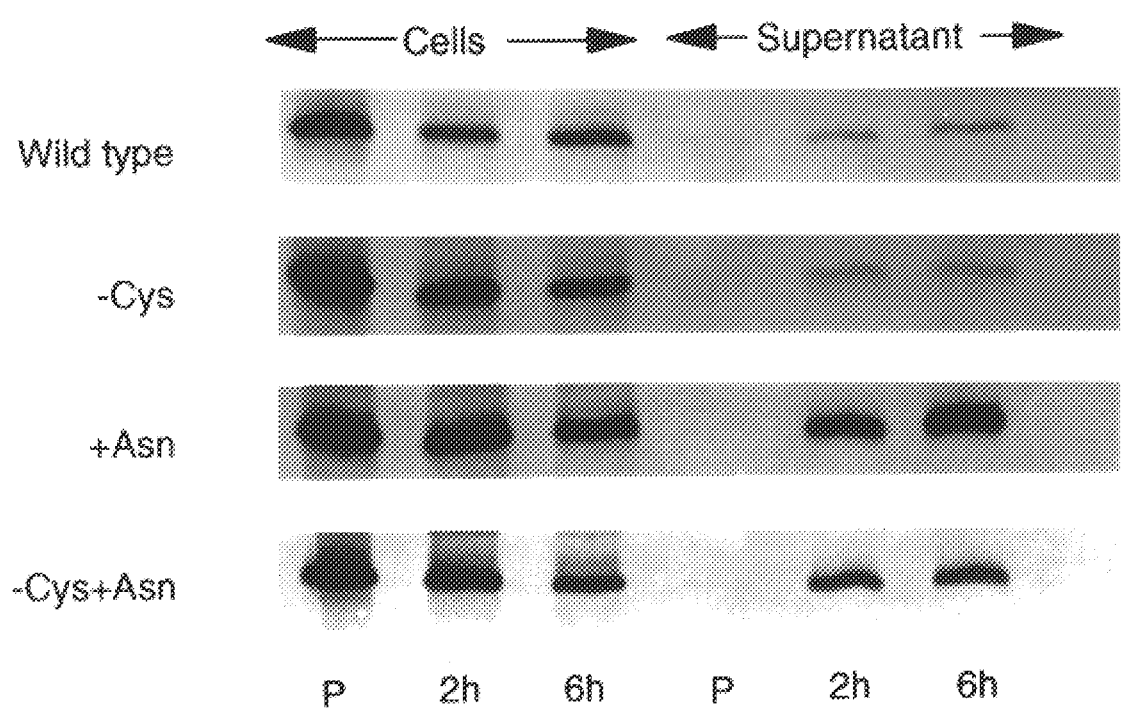

FIG. 6

| | PAGE | | % Glycosylated | |
|---|---|---|---|---|
| | Cells Pulse | Supe Chase | Cells Pulse | Supe Chase |
| OKT9 | | | 70 | 86 |
| U7.6 +Asn | | | 41 | 68 |
| U7.6 -Cys+Asn | | | 38 | 73 |

METHOD OF PRODUCING SINGLE-CHAIN FV MOLECULES

GOVERNMENT FUNDING

The invention described herein was supported in whole or in part by the National Institutes of Health. The United States Government has certain rights to this invention.

BACKGROUND OF THE INVENTION

Single-chain Fv (sFv) proteins are genetically engineered molecules that consist of the two variable domains of an antibody or T cell receptor connected by a polypeptide linker and that contain the antigen binding function of the parental protein in a single 30 kD polypeptide chain. (Huston, J. S., et al., *Proc. Natl. Acad. Sci. U.S.A.* 85:5879–5883 (1988); Bird, R. E., et al. *Science* 242:423–426 (1988); Huston, J. S., et al., *Meth. Enzymol.* 203:46–88 (1991)).

The Fv portion of an antibody is the smallest fragment to bear the complete antigen-binding site. It is a 25 kD heterodimer consisting of the N-terminal variable (V) domains of the heavy (H) and light (L) chain. (Inbar, D., et al., *Proc. Natl. Acad. Sci. U.S.A.* 69:2659–2662 (1972); Hochman, J., *Biochemistry* 15:2706–2710 (1976); Hochman, J., et al., *Biochemistry* 12:1130–1135 (1973)). More recently, a genetically engineered single-chain Fv (sFv) with antigen binding activity has been produced by connecting the C-terminus of one V domain to the N-terminus of the other with a peptide linker. Huston, J. S., et al., *Proc. Natl. Acad. Sci U.S.A.* 85:5879–5883 (1988); and Bird, R. E., et al., *Science* 242:423–426 (1988) Since then, sFv proteins have been produced from a large number of different antibodies (Huston, J. S., et al., *Intern. Rev. Immunol.* 10:195–217 (1993); Winter, G. and Milstein, C. *Nature* 349:293–299 (1991)) and initial studies (Kurucz, I., et al., *Proc. Natl. Acad. Sci. U.S.A.* 90:3830–3834 (1993); Novotny, J., et al., *Proc. Natl. Acad. Sci. USA* 88:8646–8650 (1991); Soo Hoo, W. F., et al., *Proc. Natl. Acad. Sci. USA* 89:4759–4763 (1992); Ward, E. S., *J. Mol. Biol.* 224:885–890 (1992)) have described the production of sFv analogues of T cell receptors (TcR), cell surface molecules that are highly homologous to immunoglobulins (Hedrick, S. M., et al., *Nature* 308:153–158 (1984); Davis, M. M. and Bjorkman, P. J., *Nature* 334, 395–402 (1988)).

Most sFv proteins have been generated in bacteria, often as insoluble, cytoplasmic inclusion bodies. Protein from inclusion bodies is not active and must be solubilized, renatured in vitro and oxidized to form parent disulfide bonds, (Huston, J. S., et al. *Methods Enzymol.* 203:46–78 (1991)). Alternatively the introduction of an N-terminal leader sequence can direct sFv into the periplasmic space of bacteria by a secretion process wherein the leader sequence is removed (Holland, I. B., et al., *Methods Enzymol.* 182:132–143 (1990)) and protein folding is accomplished, aided by enzymes that catalyze disulfide bond formation (Bardwell, J. C. A., et al., *Cell* 67:581–589 (1991)) and cis-trans isomerization of proline residues (Hayano, T., et al., *Biochemistry* 30:3041–3048 (1991)). However, even with these enzymes, secreted sFv proteins sometimes exist as insoluble aggregates in the periplasmic space, which must be solubilized and refolded in vitro (Johnson, S. and Bird, R. E., *Methods Enzymol.* 203:88–98 (1991); George, A. J. T., et al., *J. Immunol.* 152, in press (1994)). Knappik, A., et al. (*Bio/Technology* 11:77–83 (1993)) have recently attempted to overcome this problem by overexpressing protein disulfide isomerase and prolyl cis-trans isomerase in the piroplasm of bacteria. However, neither enzyme induced a significant change in folding efficiency of sFv proteins when expressed either alone or together with the other enzyme.

A different approach to produce active sFv would be to use the more sophisticated refolding machinery that is located in the endoplasmic reticulum (ER) of mammalian cells. The potential benefit of this approach could be substantial, since the ER not only contains enzymes that catalyze specific isomerization steps but it also contains a number of proteins (e.g., chaperones) that aid in the folding process and prevent the secretion of incorrectly folded proteins (Gething, M. J. and Sambrook, J. *Nature* 355:33–45 (1992); Pelham, H. R., *Annu. Rev. Cell Biol.* 5:1–23 (1989); Hurtley, S. M. and Helenius, A., *Annu. Rev. Cell Biol.* 5:277–307 (1989)). A number of sFv fusion proteins have been expressed in or on the surface of mammalian cells. Examples include an anti-HIV-KDEL (SEQ ID NO: 18) fusion protein, or anti-HIV sFv alone, that remains bound in the ER (Marasco, W. A., et al. *Proc. Natl. Acad. Sci. USA* 90:7889–7893 (1993)) and anti-tumor sFv proteins fused to TcR-ζ or $Fc_\epsilon RI$-γ that trigger cell mediated cytolysis (Eshhar, Z., et al. *Proc. Natl. Acad. Sci. USA* 90:720–724 (1993); Hwu, P., et al. *J. ExP. Med.* 178:361–366 (1993); Stancovski, I., et al. *J. Immunol.* 151:6577–6582 (1993)). However, production of this class of proteins by mammalian cells is generally very low, varying from a few micrograms to a few milligrams, if production is possible at all. (Davis, S. J., et al., *J. Biol. Chem.* 265:10410–10418 (1990); Traaunecker, A. et al., *EMBO J.*, 10:3655–3659 (1991)).

To date, it is not certain what the rate-limiting step, or steps, in the efficient expression and secretion of sFv proteins in mammalian cells may be, nor has it been apparent how to induce, or increase existing production levels.

SUMMARY OF THE INVENTION

The present invention relates to a method of producing single-chain Fv molecules in mammalian cells and single-chain Fv molecules produced by this method. The single-chain Fv molecules produced by this method are capable of being secreted from mammalian cells into the cell culture medium, thus greatly facilitating their isolation and purification. Importantly, the single-chain Fv molecules produced by this method are secreted as correctly folded, biologically active binding molecules capable of reacting with their respective ligands, thus eliminating the need of further in vitro manipulation to remove bacterial endotoxin and to further purify or to refold these molecules to recover biological activity.

The method described herein is based on the finding that, in the secretion of single-chain Fv molecules from mammalian cells, their exit from the endoplasmic reticulum can be rate-limiting and that glycosylation of the single-chain Fv molecules can enhance the rate of secretion.

More specifically, the parent nucleic acid sequence encoding a single-chain Fv molecule is modified by oligonucleotide-directed mutagenesis of the coding sequence to include one, or more, non-naturally occurring glycosylation site, or sites. As used herein, the term single-chain Fv molecule includes novel analogs of the single-chain Fv. These sFv analogs include, for example, the sFv' and the (sFv')2 molecules wherein a cysteine-containing peptide is fused to the sFv carboxy terminus. Another example includes a BiBABS molecule ($V_H$-$V_L$-$V_H$-$V_L$) wherein two sFv molecules are linked together. Descriptions of additional single-chain Fv molecules encompassed by this invention are found in Huston, J. S., et al. *Cell Biophysics.*, 24 in press (1994), the teachings of which are incorporated herein by reference. Also encompassed by this invention are chimeric multivalent protein analogs described in WO 93/23537, the teachings of which are also incorporated herein by reference, and antibody fragments such as Fv, Fab and Fab' fragments (Better, M. and Howitz A. H., *Enzymol.* 178:476–796 (1989)). As used herein, the term non-naturally occurring glycosylation site means a glycosylation site not encoded by the parent single-chain Fv nucleic acid sequence. The novel glycosylation site, or sites, are incorporated into the parent single-chain Fv nucleic acid sequence at an appropriate amino acid residue, or residues contained within the sequence. Preferably, the novel glycosylation site, or sites, are either N-linked (asparagine-linked) or O-linked (serine-or threonine-linked) glycosylation sites. The parent sFv coding sequence is modified in such a manner (e.g., by insertion, deletion, or substitution of nucleotides) so as to result in the consensus amino acid sequence Asn-X-Ser/Thr, which leads to N-linked glycosylation, or Ser/Thr, which leads to O-linked glycosylation. In a preferred embodiment, the novel glycosylation site(s) is(are) located in a region of the sFv protein product that is not buried within the folded protein (e.g., exposed on the protein surface at a β-turn, in a loop, or within a linker sequence).

The modified sFv nucleic acid construct (also referred to herein as the sFv construct) is introduced into a vector capable of expressing the glycosylated sFv protein construct in a eukaryotic cell. In a preferred embodiment, the eukaryotic cell is a mammalian cell. The term vector, as used herein means any nucleic acid sequence comprising a nucleic acid sequence of interest, competent to be incorporated into a eukaryotic host cell resulting in the expression of the nucleic acid sequence of interest. Vectors can include, for example, linear nucleic acid sequences, plasmids, cosmids, phagemids, and extrachromosomal DNA. Specifically, the vector can be a recombinant DNA vector. Also as used herein, the term expression, or gene expression, is meant to refer to the production of the protein product of the nucleic acid sequence of interest, including transcription of the DNA and translation of the RNA transcript. The eukaryotic host cell can be any mammalian cell capable of expressing protein, including for example, immortalized mammalian cells such as COS-7 cells, 293 cells, myeloma, Chinese hamster ovary (CHO) cells. The host cells can also be cultured yeast cells.

The vector is transfected into the eukaryotic cell, for example, by calcium phosphate precipitation, and the transfected cell is maintained under conditions sufficient for propagation of the cells, expression of the sFv construct within the cell and secretion of the sFv protein product into the cell culture medium. For example, if a mammalian cell is the transfected host cell, the cell is cultured in suitable culture medium and under an atmosphere conducive for growth of the cell. As the host cell grows, the vector integrates into the host cell genome and expresses the sFv construct within the host cell resulting in the sFv protein product. Importantly, this sFv protein product contains at least one novel, engineered glycosylation site that was not present in the parent sFv molecule. This new glycosylation site signals the attachment of oligosaccharide (carbohydrate) chains to the sFv protein, which takes place within the endoplasmic reticulum (ER) of the eukaryotic cell. Under the conditions described herein, glycosylated sFv proteins are secreted from the ER at an increased rate relative to the rate of secretion of parent sFv proteins. Importantly, the secretable, glycosylated sFv molecules described herein, typically exhibit biological activity and properties which have not been previously accessible through bacterial (prokaryotic) expression or secretion. Additionally, glycosylation of CDRs in some antibodies can be important to improve binding, especially to carbohydrate antigens (Wright, A. and Morrison, W., in SPRING SEMINARS IN IMMUNOLOGY 15:259–273 (1993)),. Thus specific or random introduction of glycosylation sites into CDRs of sFv proteins, as described by the present invention can be of value.

The present invention further relates to modified secretable sFv proteins having one, or more, non-naturally occurring glycosylation site(s), and to the DNA sequences encoding these proteins. More specifically, these proteins have at least one N-linked or O-linked glycosylation site that is not encoded by the parent sFv protein. These modifications are also referred to herein as post-translational modifications. Although these sFv proteins are modified to contain non-naturally occurring glycosylation sites, they retain the same specificity of binding as exhibited by the parent, unglycosylated sFv protein.

Thus, as a result of the method described herein, post-translationally modified sFv molecules capable of specifically binding ligand can be successfully produced in and secreted from eukaryotic cells.

BRIEF DESCRIPTION OF THE DRAWINGS

FIG. 2A shows the nucleic acid sequence (SEQ ID NO: 14) an encoded amino sequence (SEQ ID NO: 15) of the $V_H$ region of U7.6 sFv.

FIG. 2B shows the nucleic acid sequence (SEQ ID NO: 16) and the encoded amino acid sequence (SEQ ID NO: 17) of the $V_L$ region of U7.6 sFv.

FIG. 3A is an electrophoretic gel showing the distribution of sFv in COS-7 cells and culture supernatant at different times in a pulse chase experiment.

FIG. 5A is an electrophoretic gel showing the presence of U7.6 sFv mutants in cells and supernatant in a pulse chase experiment.

FIG. 6 is an electrophoretic gel showing the preferential secretion of glycosylated forms of sFv proteins from tunicamycin-treated cells.

DETAILED DESCRIPTION OF THE INVENTION

Figure 1:
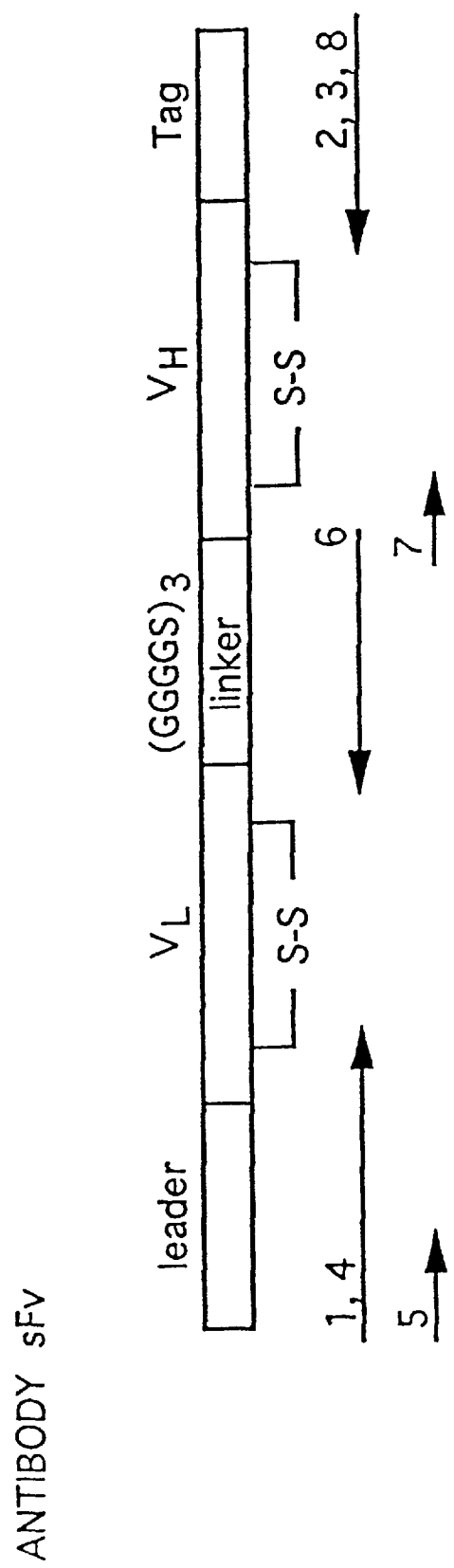
FIG. 1 is a diagrammatic representation of the sFv gene constructs.
Figure 3B:
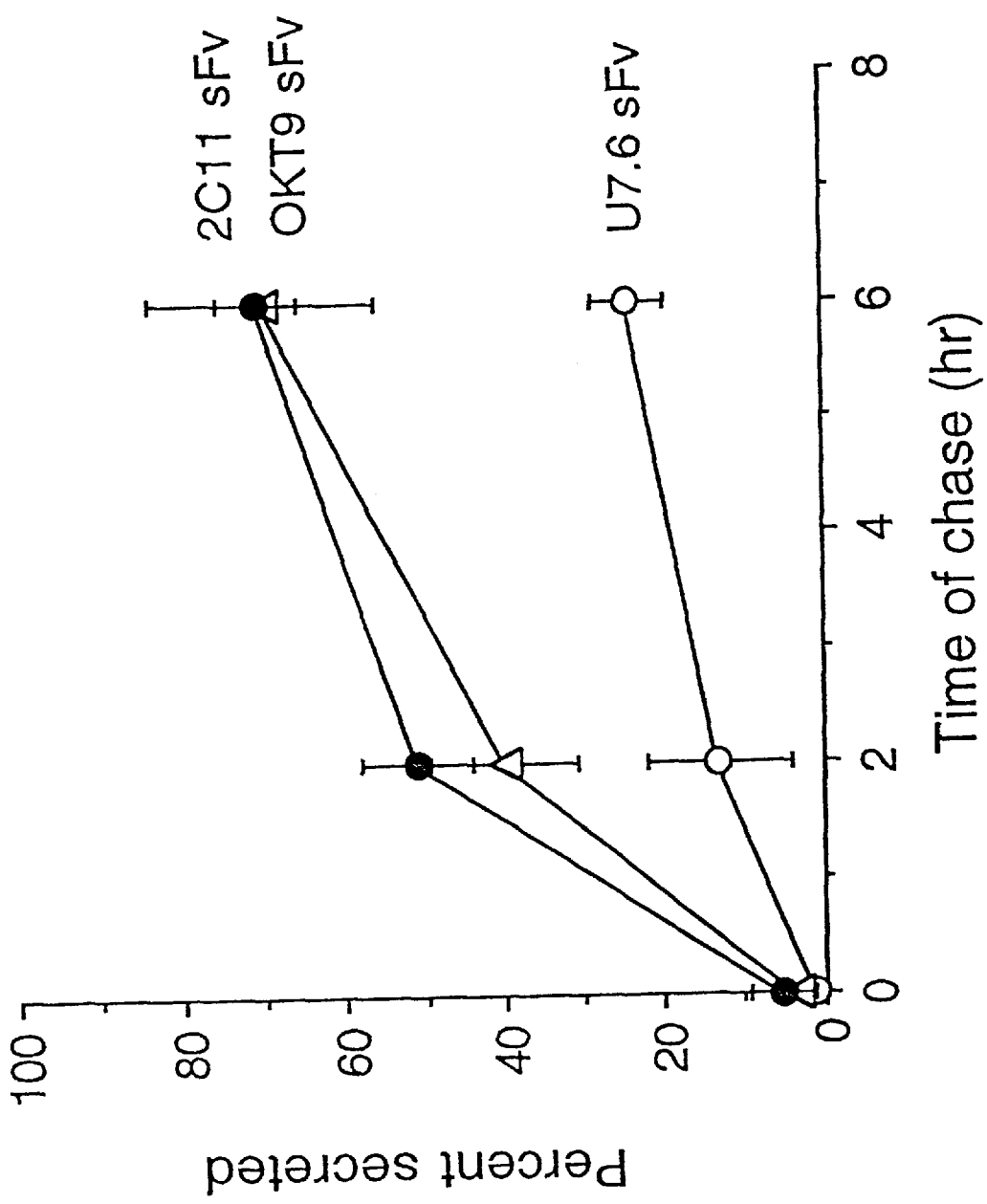
FIG. 3B is a graphic representation showing the rate of secretion of the different sFv molecules.
Figure 4:
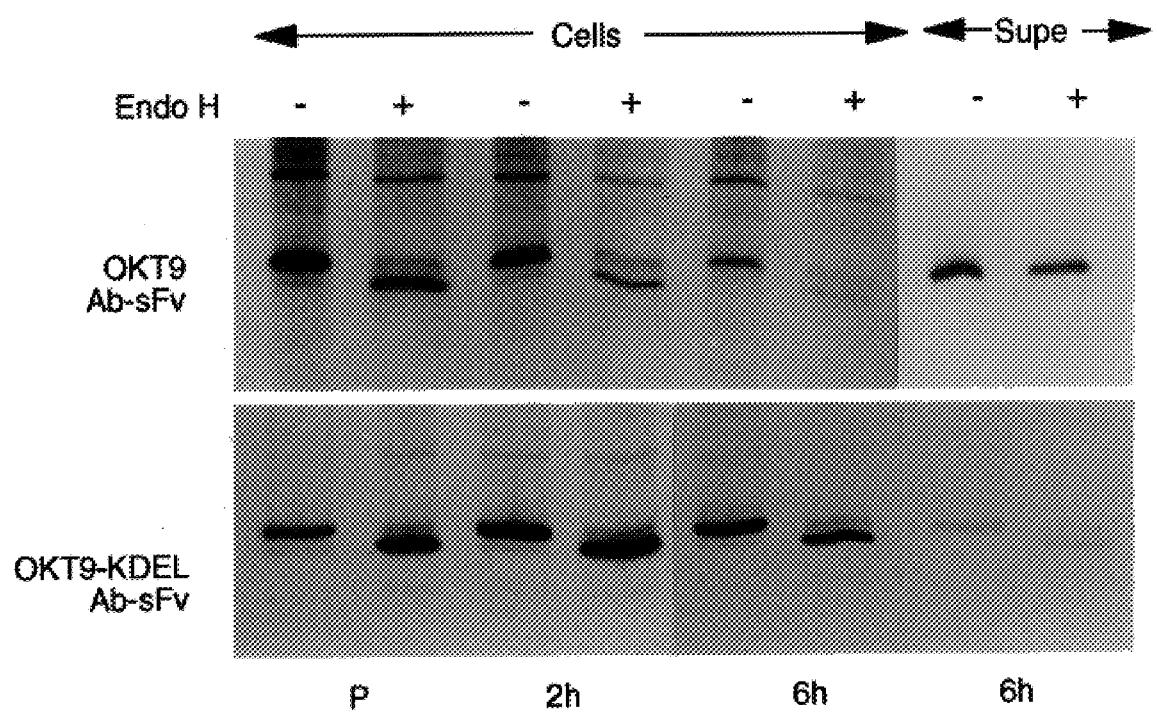
FIG. 4 is an electrophoretic gel showing the processing of N-linked carbohydrate during sFv secretion.

The invention described herein relates to a method of producing single-chain Fv molecules in eukaryotic cells and single-chain Fv molecules produced by this method. Specifically, the invention relates to a method of producing single-chain Fv proteins that are capable of being secreted from mammalian cells directly into the cell culture medium. Importantly, these single-chain Fv proteins are secreted as correctly folded, biologically active binding molecules, capable of binding ligand with specificity.

The method described herein is based on the finding that, in the secretion of single-chain Fv proteins from mammalian cells, their exit from the endoplasmic reticulum can be rate-limiting and that glycosylation of the single-chain Fv protein can enhance rates of secretion.

A wide variety of proteins are secreted by vertebrate cells. In fact, some cells are highly specialized to secrete specific proteins, such as B-lymphocytes that secrete immunoglobulins. Ribosomes that synthesize secreted proteins are bound to the endoplasmic reticulum (ER). After synthesis these proteins are translocated into the lumen of the ER and then move in small transport vesicles through the Golgi complex and eventually exit the cell. This entire process is often termed protein maturation.

Specific maturation steps known to occur in the ER include proteolytic cleavage of leader sequences, addition and modification of carbohydrate residues, formation of disulfide bonds, and the folding of the nascent polypeptide chain into its correct three-dimensional structure. The first two processes occur very rapidly with all proteins, and for example, with antibodies, the formation of disulfide bonds occurs as the peptide passes into the lumen of the ER. (Bergman, L. W. and Kuehl, W. M., *J. Biol. Chem.* 254:8869–8876 (1979)).

In the case of antibodies, nascent heavy (H) and light (L) chains are known to bind to chaperones, proteins resident in the ER that facilitate the folding and assembly of H and L chains into functional antibodies. Both chains associate with heavy chain binding protein (BiP or GRP78) (Knittler, M. R. and Haas, I. G. *EMBO J.* 11:1573–1581 (1992)) and GRP94 (Melnick, J., et al. *J. Biol. Chem.* 267:21303–21306 (1992)) during folding and assembly, and IP90, another putative chaperone, interacts with partial complexes of membrane immunoglobulin in the ER of B-cells (Hochstenbach, F., et al. *Proc. Natl. Acad. Sci. U.S.A.* 89:4734–4738 (1992)). Once antibodies have assumed their proper configuration they dissociate from the chaperones and proceed through the Golgi on their way to being secreted. In the case of sFv proteins, little is known about protein folding. One recent report discussed a non-secretable sFv (i.e., an sFv which was produced but not secreted by mammalian cells) that interacted with BiP. (Marasco, W. A., Haseltine, et al. *Proc. Natl. Acad. Sci. USA* 90:7889–7893 (1993)). Another report discussed that the $V_H$ domain contributes to the binding of immunoglobulin heavy chains to BiP. (Pollak, B. A., et al. *Proc. Natl. Acad. Sci. U.S.A.* 84:9199–9203 (1987)).

Moreover, many antibodies, other secreted proteins and most cell surface proteins are glycosylated. That is, they have oligosaccharides covalently linked to amino acid residues. (Machamer, C. E. and Rose, J. K., *J. Biol. Chem.* 263:5948–5954 (1988)). Many potential functions have been suggested for these oligosaccharides, including assistance with polypeptide folding, prevention of intracellular aggregation, protection from proteolytic breakdown and signals for intracellular targeting and cellular recognition. (Olden, K. et al., *Biochem. Biophys. Acta* 650:209–232 (1992)). As described herein, it is now demonstrated that mammalian cells transfected with different sFv genes secrete the corresponding active sFv molecules at different rates and that glycosylation can affect these secretion rates.

A nucleic acid sequence encoding a single-chain Fv (sFv) protein can be modified to include one, or more non-naturally occurring N-linked, or O-linked glycosylation site (s). The unmodified nucleic acid sequence encoding the sFv protein is referred to herein as the parent sFv nucleic acid sequence. As used herein, the term non-naturally occurring glycosylation site means a glycosylation site that is not encoded for in the parent nucleic acid sequence. Thus, the modified sFv protein contains at least one glycosylation site that is not encoded by the parent nucleic acid sequence.

sFv proteins suitable for modification by the method described herein, include single-chain antibody proteins, such as U7.6, other Ig superfamily analogues, such as the T-cell receptor protein and chimeric derivatives of these sFv proteins. A detailed description of sFv molecules is found in U.S. Pat. Nos. 5,091,513, issued Feb. 25, 1992, and 5,132, 405, issued Jul. 21, 1992, the teachings of which are incorporated herein by reference. A description of chimeric single-chain protein analogues is found in International Patent Application, WO 93/23537, the teachings of which are incorporated by reference. References to nucleic acid sequences and constructions of sFv molecules are described, for example, in Huston, J. S., et al., *Intern. Rev. Immunol.* 10:195–217 (1993). The sFv proteins encompassed by this invention also include sFv fusion proteins where effector domains are fused to either chain terminus of the sFv, as described, for example, in Huston, J. S., et al., *Meth. Enzymol.* 203:46–88 (1991).

Nucleic acid sequences encoding single-chain Fv proteins, Ig superfamily analogues, chimeric proteins, sFv fusion proteins and other sFv protein species can be modified, as described in Example 1, by oligonucleotide-directed mutagenesis of the coding sequence to include one, or more, glycosylation site(s) that are not present in the parent sequence. The modified nucleic acid sequence encoding an sFv protein containing at least one novel gylcosylation site that was not encoded by the parent nucleic acid sequence is referred to herein as the modified sFv nucleic acid sequence, or sFv construct.

N-linked (asparagine-linked) sites are the preferred sites of glycosylation contemplated by this invention. The parent sFv coding sequence is altered in such a manner (e.g., by addition, deletion, or substitution of nucleotides) so as to result in a nucleic acid sequence that encodes the consensus amino acid sequence Asn-X-Ser/Thr. This consensus sequence signals an N-linked glycosylation site.

However, O-linked glycosylation sites are also encompassed by this invention. If an O-linked glycosylation site is inserted, the parent sFv nucleic acid sequence is altered so as to result in a modified nucleic acid sequence that encodes the amino acid sequence Ser/Thr. This consensus sequence signals an O-linked glycosylation site.

The selection of the novel glycosylation site, or sites, is based on the combination of the primary nucleic acid sequence encoding the sFv molecule and the local tertiary structure in the parent protein, which can, for example, represent a β-turn or loop structure. (Aubert et al, *Arch. Biochem. Biophys.* 175:410 (1976)). The novel glycosylation site(s) is(are) located in a region of the protein that is not expected to be buried within the folded protein, nor sequestered at the $V_H$-$V_L$ interface. That is, the novel glycosylation site is attached to an amino acid residue that is exposed on the protein surface. For example, the presence of an N-linked glycosylation site in the first framework region of $V_H$ of two sFvs (OKT9 Ab-sFv, and U7.6Ab-sFv) increases their rate of secretion without significantly altering their antigen binding affinities. If more than one glycosylation site is added, the sites can be constructed to be adjacent to each other, (e.g., attached to adjacent amino acid residues located within the amino acid sequence) or they can be interspersed at various/random positions within the sequence (e.g., attached to non-adjacent amino acid residues of the sequence).

The modified sFv nucleic acid construct is then introduced into a vector capable of expressing the modified construct in a host cell as described in Example 2. Such vectors, especially recombinant DNA vectors, are well known to those skilled in the art. These vectors supply a promoter and other elements necessary to express the construct in eukaryotic cells. Specifically, plasmid vectors are contemplated for use in the present invention, which include both prokaryotic sequences and mammalian transcription units, such as described in MOLECULAR CLONING: A LABORATORY MANUAL, 2d Ed. Sambrook, J., et al., eds., Cold Spring Harbor Laboratory Press, N.Y., (1989).

The vector is then introduced into a host cell by methods known to those of skill in the art. Introduction of the vector into the host cell can be accomplished by any method that introduces the construct into the cell, including, for example, calcium phosphate precipitation, microinjection, or electroporation. See, e.g., Cockett et al., *Bio/technology*, 8:662–667 (1990); CURRENT PROTOCOLS IN MOLECULAR BIOLOGY, Ausubel, F. M., ed., John Wiley & Sons, N.Y. (1989)). For example, as described in Example 2, a mammalian cell is used as the host cell. The mammalian cell can be transfected using the calcium phosphate method. The transfected host cell is maintained under conditions sufficient for propagation of the cell and expression of the sFv construct within the cell. Host cells can include, for example, immortalized mammalian cells such as COS-7 cells, 293 cells, myeloma or Chinese hamster ovary (CHO) cell lines, and cultured yeast cells. Conditions sufficient for propagation of the cell and expression of the sFv construct include any type of culture system and media known to those of skill in the art suitable for the propagation of the host cell. Such culture systems include microcarrier or hollow fiber culture systems, as well as suspension systems, cultured under optimal conditions of media, atmosphere and temperature. As the host cell grows, the vector, for example, integrates into the host cell genome and expresses the sFv construct within the host cell resulting in the sFv protein product.

Importantly, the expressed sFv construct protein product contains at least one novel glycosylation site that is not encoded by the parent sFv sequence. Within the endoplasmic reticulum (ER) of the mammalian cell oligosaccharide (carbohydrate) chains are attached to the sFv protein at these glycosylation sites and the sFv protein is folded into its biologically active conformation. These correctly folded, glycosylated sFv proteins are then transported from the ER to the cell surface and secreted from the cell. Key to this method is the fact that, under the conditions described herein, sFv molecules with one, or more, non-naturally occurring glycosylation sites are secreted from the cell at a faster rate relative to the secretion rate of unglycosylated sFv molecules, and that these glycosylated sFv molecules retain their biological activity.

The secretion of sFv molecules into cell culture medium as biologically active, soluble proteins greatly facilitates their isolation and purification. Most current strategies used to produce sFv molecules have relied on bacterial expression of fusion proteins. (Huston, J. S., et al., *Meth. Enzymol.* 203:46–88 (1991)). sFv proteins produced in bacterial culture often contain bacterial endotoxin which contaminates the protein and requires further purification procedures to produce clinically acceptable proteins. Moreover, if periplasmic secretion methods do not produce active sFv, fusion proteins may be secreted or expressed in bacterial cells as insoluble inclusion bodies which require further solubilization and refolding to obtain biologically active proteins. In most cases, denaturants such as SDS, urea, or guanidine HCl have to be used to extract the inclusion body sFv protein. Subsequently, the protein has to be renatured (i.e., correctly folded) to achieve biological activity and this may prove difficult, if not impossible. (PRINCIPLES OF GENE EXPRESSION, 4th Ed., Old, R. W. and Primrose, S. B., eds., Blackwell Scientific Publications, Cambridge, Mass. (1989)). In the case of binding proteins, e.g., a protein such as an sFv protein, folding to achieve the correct three-dimensional conformation is a prerequisite of its biological activity.

In addition to correct folding to achieve biological activity, many different post-translational modifications have been described as necessary for active proteins. (PRINCIPLES OF GENE EXPRESSION, 4th Ed., Old, R. W. and Primrose, S. B., eds., Blackwell Scientific Publications, Cambridge, Mass. (1989)). Besides N- and O-linked glycosylation, these modifications include phosphorylation, acetylation, amidation, sulphuration, attachment of fatty acids and the formation of unusual amino acids. These post-translational modifications are not known to occur in bacteria. Some glycosylation has been reported in yeast and in baculovirus cells, however, the composition and sequences of the resulting oligosaccharide chains can differ significantly from those found in mammalian cells. Thus, expression and secretion of sFv molecules in mammalian cells, as described herein, provides a rapid and efficient method of producing biologically active sFv molecules. The sFv protein produced by the described method can be isolated, purified and tested for biological activity using known laboratory techniques, such as described in Examples 3 and 4. For example, if the sFv protein is an antibody sFv, the biological activity can be tested by immunoprecipitation, ELISA, or radioimmunoassay. Furthermore, testing biological activity of the sFv protein produced by the method described herein is greatly facilitated because the sFv protein is secreted in soluble form, directly into the cell culture medium. It is simply a matter of obtaining an aliquot of culture medium to test the activity of the sFv protein directly without further manipulation.

The present invention also relates to modified, secretable sFv proteins having one, or more, non-naturally occurring glycosylation site(s) and to the DNA sequences encoding these modified sFv proteins. Additional advantages are achieved by producing glycosylated sFv molecules. Non-glycosylated proteins can be subject to aberrant aggregation such as that mediated by non-covalent association (McCoutney et al., *Protein Eng.*, (1994) or intermolecular disulfide bonding. (Machamer, C. E. and Rose, J. K., *J. Biol. Chem.* 263:5955–5960 (1988)). For example, as protein accumulates in the ER, cysteine residues in neighboring proteins can cross-link to form multimers. This results in large aggregates of protein which can be difficult to disassociate in order to further isolate and purify the protein. Alternate types of aggregation can involve non-covalent self-association, as for the first example, mediated by the bottom surface of an sFv, sFv analog or an antibody fragment, which is diametrically opposite to the antigen combining site. This can result in an equilibrium mixture of monomers, dimers and even higher aggregates. Oligosaccharide chains positioned at specific amino acid residues in the proteins can play an important role in the prevention of aggregation and non-covalent association.

Figure 5B:
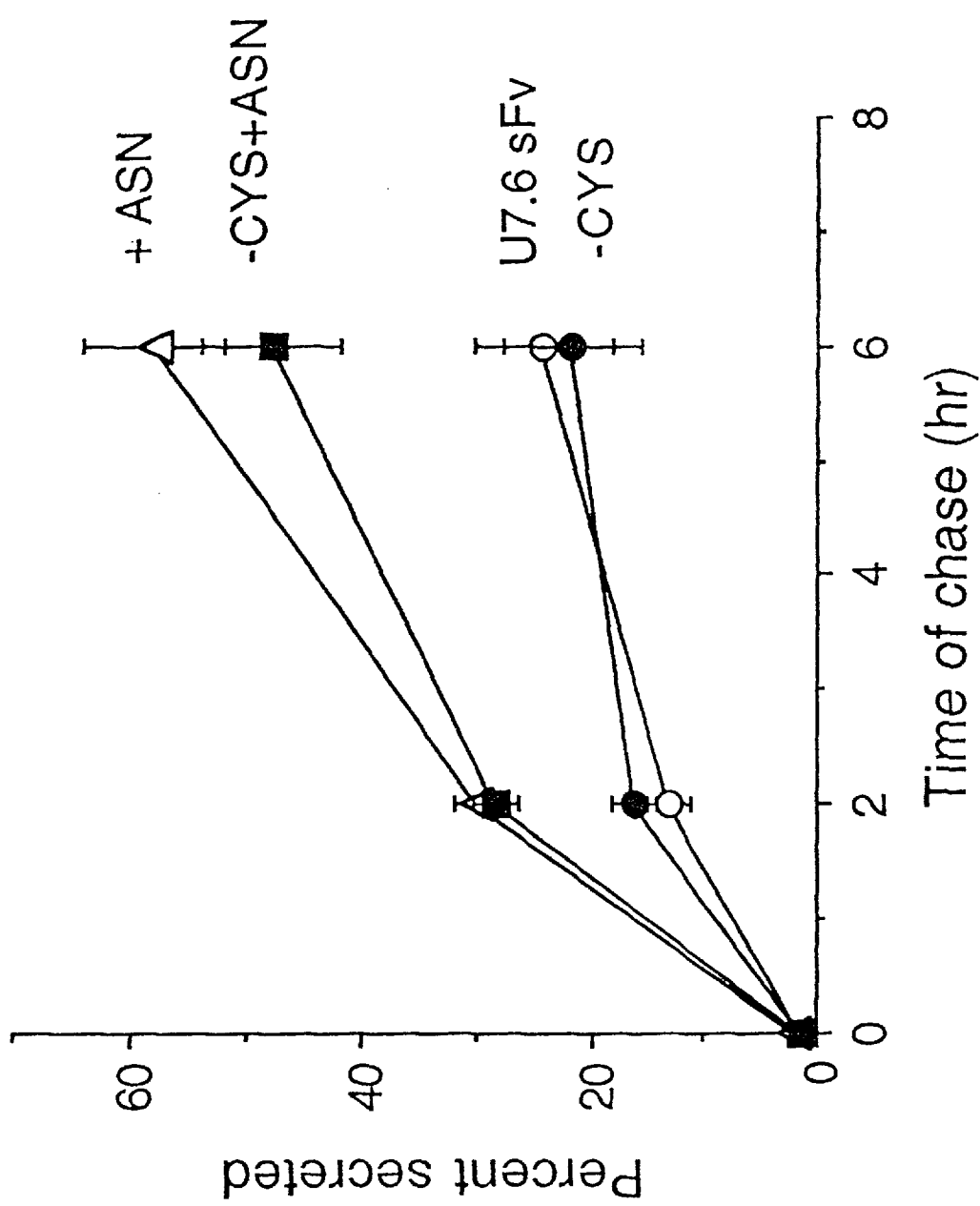
FIG. 5B is a graphic representation showing the densitometric analysis of the data shown in FIG. 5A. sFv present in the supernatant is plotted as percent of total immunoprecipitation material.

In clinical applications, the presence of oligosaccharide chains can protect the protein from proteolytic degradation, resulting in increased circulating half-life of the protein. (Goto, M, et al., *Bio/Technology*, 6:67–71 (1988)). The presence of an oligosaccharide chain, terminating in sialic acid, can also modify the in vivo biodistribution, pharmokenetics, elimination and/or renal uptake of a single-chain Fv molecule. For example, if the terminal sialic acid is removed, the remaining carbohydrate chain residue can be a residue recognized by hepatic receptors, thus signaling elimination. If a sialic acid residue is present, the signal for elimination can be blocked, again resulting in longer circulating half-life of the protein. Thus, the present invention provides a method of modifying the pharmokenetics of sFv proteins in the body.

The attachment of oligosaccharide chains can also decrease the antigenicity of the sFv molecule. For example, the linker sequence used in an sFv molecule to connect $V_H$ and $V_L$ could elicit an antigenic response to the sFv molecule. The addition of a glycosylation site within the linker can prevent the unwanted response, or decrease the severity of the response by masking the antigenic amino acid residues responsible for the response.

sFv Constructs

To evaluate sFv production in mammalian cells, COS-7 cells were transfected with vectors encoding four different sFv molecules; U7.6-sFv directed against the hapten DNP, OKT9-sFv against the human TfR, 2C11-sFv against the murine CD3-$\epsilon$ chain, and 2B4, a TcR-sFv that recognizes a cytochrome C peptide bound to I-$E^k$. These sFv molecules are described in detail in Example 1. Light chain leaders were used to direct newly-synthesized Ab-sFv proteins to the endoplasmic reticulum, and a c-myc peptide sequence was introduced at the 3' end of each Ab-sFv construct to facilitate detection of the proteins. The three Ab-sFv proteins contained a $(G_4\text{-}S)_3$ linker connecting the 3' end of $V_L$ with the 5' end of $V_H$, as shown in FIG. 1. OKT9-sFv is exceptional in that it has an N-linked glycosylation site located at position 19 in FR1 of $V_H$. The U7.6 antibody also differs from the other Ab-sFv proteins in that it has an extra cysteine in $V_L$, located in CDR3, 3 amino acid residues C-terminal to the second domain-forming cys, as shown in FIG. 2A and 2B. The TcR-sFv construct contained a $V_\alpha$ leader sequence, $V_\alpha$, and a linker consisting of 14 amino acid residues of $C_\alpha$ followed by two additional residues resulting from a Pst I site. This joined $V_\beta$ and 7 $C_\beta$ residues. The 2B4 sFv has three glycosylation sites, one in $V_\alpha$, one in $V_\beta$ and one in $C_\beta$, and two additional cysteine residues in the third framework portion of $V_\beta$.

Production and secretion of sFv molecules Transfected COS-7 cells were labeled as described in detail in the Example 2, with [$^{35}$S]-met for 60 min and then chased with unfolded methionine for either 0, 2, or 6 h. The sFv secretion products were then precipitated from both the cell lysates and the negative supernatants using mouse antibody to the C-terminal myc peptide tag and rabbit anti-mouse Ig bound to Protein A-Sepharose. FIG. 3A and 3B shows the results of the production and secretion of sFv in COS-7 cells. FIG. 3A shows the distribution of sFv in cells and culture supernatant at different times during a pulse chase experiment. COS-7 cells were transfected with plasmid DNA encoding the indicated sFv and 48 h later pulsed for 1 h with [$^{35}$S]-methionine- Cells were subsequently chased for 0 ("P" in the figure), 2 or 6 h as indicated. The sFv proteins were immunoprecipitated, subjected to SDS-PAGE under reducing conditions, and visualized by autoradiography. FIG. 3B shows the rate of secretion of the different sFv molecules. Autoradiograms were quantified by densitometry. Total amounts of sFv in cell lysate and supernatant were determined and the percentage of total sFv present in the supernatant at each time point was calculated and plotted. Both OKT9 and 2C11 sFv proteins were secreted from the cells at similar rates, culminating in most sFv being present in the medium after a 6 h chase.

By contrast, the U7.6-sFv was secreted much more slowly, with only a minor amount being present in the medium after the 6 h chase. The 2B4 TcR-sFv was handled differently by the COS cells than the Ab-sFv proteins, as most of this sFv could not be found in the supernatant, even after a 6 h chase. Data from three comparable independent experiments were quantified by densitometry and the percentages of total sFv in the supernatant were calculated and plotted (FIG. 3B). The percentages of sFv present in the supernatant at various times are comparable for the 2C11 and OKT9-sFv proteins, resulting in about 70% secretion after a 6 h chase. At this time only 25% of the U7.6 sFv and 5% of the 2B4-sFv were secreted in corresponding experiments.

Exit from the ER is the rate limiting step in OKT9-sFv secretion

The transfer of OKT9 and 2B4-sFv proteins from the ER to the Golgi complex was followed by measuring the acquisition of endo H resistance that is conferred on N-linked oligosaccharides by additional changes in glycosylation that occur in the Golgi. Transfected COS-7 cells were pulse labeled and chased. sFv and immunoprecipitates were either treated or not treated with endo H prior to SDS-PAGE analysis, as described in Example 3. FIG. 4 shows that the major fraction of cell-associated OKT9 sFv remained sensitive to endo H at all time points, while OKT9 sFv present in the medium was always endo H resistant. Endo H resistance was used to determine the localization of sFv in COS-7 cells at different times following pulse-labeling. Immunoprecipitates were either not treated (–) or treated (+) with endo H prior to analysis by SDS-PAGE. Samples indicated by "Cells" represent immunoprecipitates from cell-associated material at the designated times; samples indicated "Supe" are immunoprecipitates from culture supernatants 6 h after the pulse labeling.

The fact that most cell-associated OKT9-sFv was endo H sensitive indicated that it had not yet passed through the Golgi complex, and was therefore located in the ER. As a control, OKT9KDEL (SEQ ID NO: 18) sFv, which contains an ER retention signal, mostly remained cell associated and endo H-sensitive at all time points (FIG. 4). The small amount of sFv reaching the medium from these cells was endo H-sensitive, suggesting that it was released directly into the medium from the ER, most likely as a result of cell death. The 2B4 TcR-sFv behaved quite differently from the OKT9. This protein remained cell-associated and endo H-sensitive at all time points (FIG. 4), and was never secreted. Unlike the OKT9-KDEL (SEQ ID NO: 18) sFv, the glycosylation pattern of the 2B4-sFv changed with time.

Introduction of a glycosylation-site in the U7.6 sFv enhances its secretion rate The U7.6 sFv was secreted much more slowly than the other antibody sFv constructs. In order to find the source of this defect, two mutations were introduced into the U7.6-sFv, as described in Example 1. First, the extra cysteine present in CDR 3 of $V_L$ (–CYS in FIG. 5A and 5B) was removed, and secondly an N-linked glycosylation site was introduced in the same position as the glycosylation site in OKT9 (+Asn). FIG. 5A shows SDS-PAGE analysis of immunoprecipitates from cell lysates and culture supernatants from COS cells transfected with mutated U7.6 sFv proteins at different times during a pulse chase experiment. FIG. 5B shows a densitometric analysis of the data shown in FIG. 5A plotted as percent of immunoprecipitated material present in the culture supernatant.

A third construct incorporated both mutations (−Cys+Asn). COS-7 cells were transfected with the U7.6 mutants, and pulse chase experiments were performed. The data from three independent experiments were quantified and the percentages of total sFv in the supernatant were calculated and plotted in FIG. 5B. The removal of the extra cysteine residue did not result in a change in secretion level. However, the introduction of a glycosylation site both in the presence (+Asn) and absence (−Cys+Asn) of the additional cysteine markedly enhanced the rate of sFv secretion; after 6 hr, 20–25% of the non-glycosylated sFv proteins were present in the medium, as compared with 50–60% of the glycosylated proteins. Endo H experiments indicated that U7.6 +Asn and U7.6 −Cys+Asn were indeed glycosylated and that the rate limiting step in their secretion was the exit of the proteins from the ER, similar to OKT9-sFv.

To confirm the implication that glycosylation of the sFv proteins enhanced their rates of secretion, COS-7 cells transfected with the OKT9, U7.6+Asn and U7.6−Cys+Asn sFv constructs were treated with suboptimal concentrations of tunicamycin, as described in Example 2. Matched plates of transfected COS-7 cells were pretreated for 2 h; pulsed for 1 h, and chased for 2 h, all in the presence of 3 pg/ml tunicamycin. The sFv proteins were immunoprecipitated from cell lysates and analyzed by SDS-PAGE immediately after the pulse step (Cells/Pulse), and secreted sFv proteins were analyzed after a 2 h chase (Supe/Chase). On the right of FIG. 6, the percentages of immunoprecipitated sFv proteins that were glycosylated are noted, as determined by densitometry, and based on the quotient of density of the higher Mr band divided by the sum of both bands' densities.

As shown in FIG. 6, after pulsing with $^{35}$S-methionine, the immunoprecipitated sFv proteins migrated as two bands corresponding to glycosylated and non-glycosylated forms. After a 2 hr chase, there was an enrichment of the glycosylated, relative to the non-glycosylated band in supernatants from all three transfectants. Thus, glycosylation accelerates the rate of secretion of both U7.6 and OKT9-sFv proteins.

Secreted antibody sFv proteins specifically bind antigen To determine if secreted sFv proteins were active, the ability of radiolabeled material from the medium of transfected COS-7 cells to specifically bind antigen was tested as described in Example 4. Each radiolabeled sFv present in 6 h chase media was tested for antigen binding activity. For OKT9 and 2C11-sFv proteins, cells bearing the relevant antigen were incubated for 4 h at 4° C. with sFv in the presence or absence of an inhibiting antibody. The cells were subsequently washed, lysed, and bound sFv immunoprecipitated and analyzed by SDS-PAGE under reducing conditions. The reactivity of U7.6 sFv (wild type) was assessed by incubating DNP-Sepharose beads with the radiolabeled chase media for 16 h at 4° C. in the absence or presence of 1 mM DNP-ε-aminocaproate. The beads were subsequently washed, boiled in SDS-loading buffer, and eluted material was analyzed by SDS-PAGE under reducing conditions and the bands were quantified by densitometry.

Figure 7:
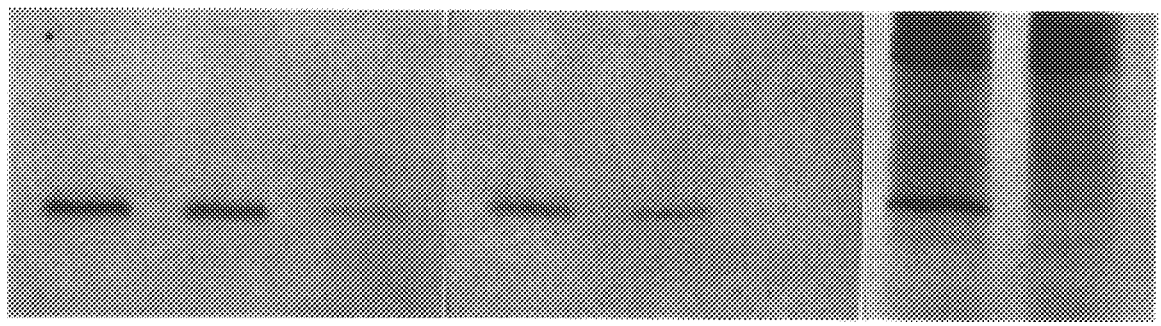
FIG. 7 is an electrophoretic gel showing that secreted sFv proteins specifically bind their antigen.

FIG. 7 shows that all three sFv proteins were indeed active; OKT9-sFv bound to K562 cells, which express high levels of human TfR, binding was inhibited by intact OKT9 antibody, but not by W6/32, an antibody that recognizes MHC Class I molecules on these cells. Similarly, 2C11 sFv bound to 2B4 cells, which are CD3$^+$, and the binding was totally inhibited by 2C11 whole. antibody but only slightly inhibited by H57, an antibody that recognizes the β chain of the TcR. Finally, U7.6 and the three U7.6 sFv mutants bound to DNP-Sepharose beads in the absence, but not in the presence of inhibiting hapten.

Sequential depletion experiments were done to determine the percentages of secreted sFv that had antigen binding activity. After two sequential incubations with DNP beads, 87–96% of the secreted U7.6-sFv constructs were specifically absorbed to the beads.

Similar experiments using multiple sequential incubations of secreted OKT9-sFv with K562 cells indicated that the vast majority of this sFv was also functional, that is, specifically bound antigen.

Figure 8:
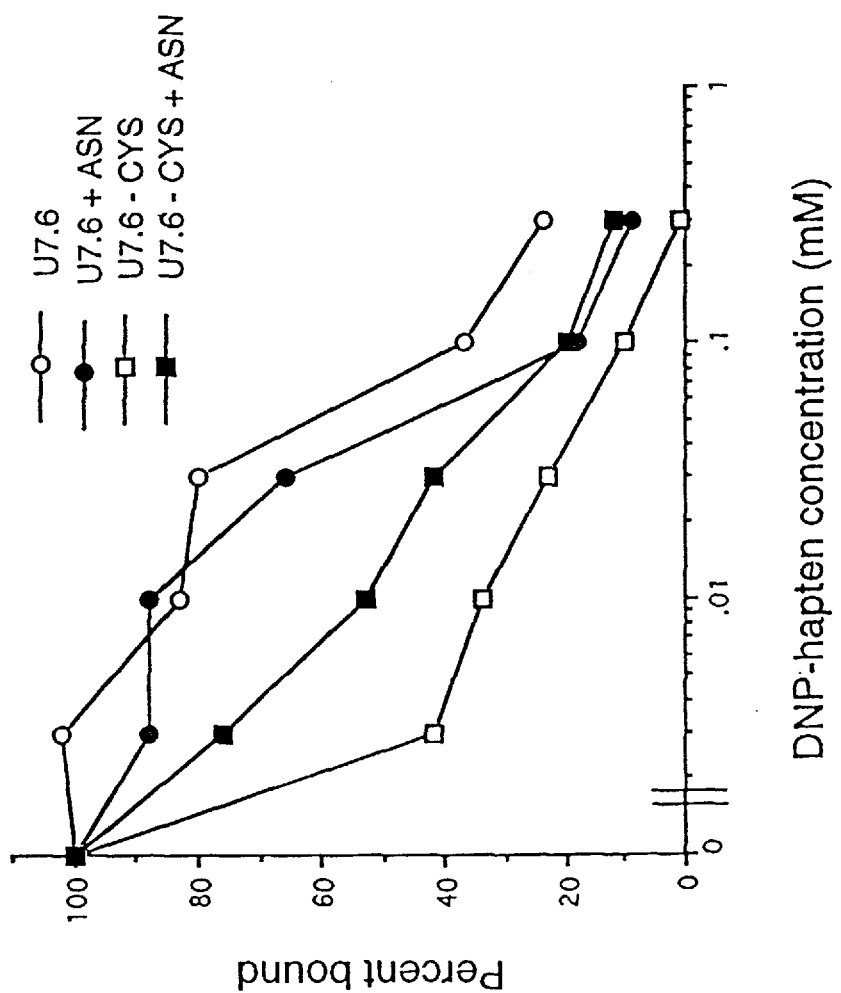
FIG. 8 is a graphic representation showing the results of experiments demonstrating the inhibition of binding of U7.6 sFv mutant proteins by DNP-hapten.

To determine if the introduced mutations have any effect on the binding affinities of the U7.6-sFvs, the binding of $^{35}$S-methionine labeled U7.6-sFv constructs to DNP-beads was inhibited with increasing amounts of DNP hapten as described in Example 4. A shown in FIG. 8, the greatest changes in affinity resulted from removal of cys 91$_L$: inhibition of binding required about 10 fold less hapten for the −Cys mutants than for the +Cys, suggesting that the affinity for hapten increased about 10 fold on removal of cys 91$_L$. Introduction of a glycosylation site at position 19 in FR' of V$_H$ in the +Cys mutants had no significant effect on binding activity, while it caused an approximately 4-fold decrease in affinity in the −Cys mutants. Thus, introduction of an N-linked glycosylation site had only a small effect on the binding activity of U7.6-sFv.

Figure 9:
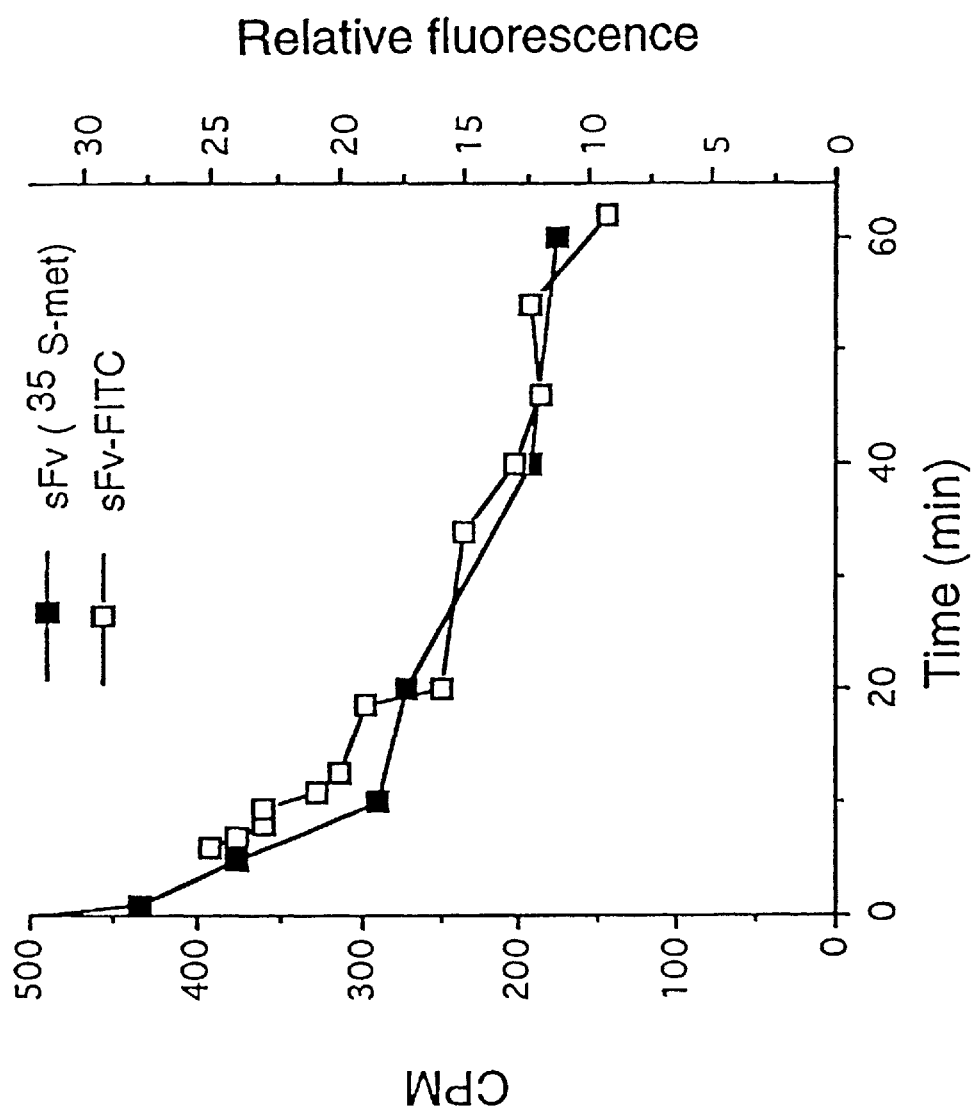
FIG. 9 is a graphic representation showing the results of experiments demonstrating that OKT9-sFvs produced in mammalian cells and bacteria dissociate from K562 cells with similar rates.

The effect of glycosylation on the binding affinity of OKT9-sFv was assessed by comparing dissociation rates of bacterially produced (and therefore non-glycosylated) and refolded sFv with that of OKT9-sFv secreted from COS-7 cells. FIG. 9 shows that the two products dissociate from K562 cells with very similar rates, suggesting that they have similar affinities for the TfR, as described in Example 5.

The amount of OKT9-sFv secreted by the transfected COS-7 cells was estimated by inhibiting its binding to the TfR with unlabeled OKT9 Fab, which binds with essentially the same affinity as the bacterially produced OKT9-sFv. By this assay, it is estimated that a COS cell supernatant contained about 0.17 μg/ml of $^{35}$S-methionine labeled OKT9-sFv.

Thus, as described herein, transfected mammalian cells can secrete active antibody sFv at different rates, and the rate of secretion can be governed by glycosylation. In pulse chase experiments, the bulk of ell-associated Ab-sFv remained in an endo H-sensitive form during a period when substantial amounts of sFv were accumulating in the medium in an endo H-resistant form. This indicates that most of the cell-associated sFv had not yet passed through the medial Golgi, where carbohydrate modifications conferring endo H resistance occur (Dunphy, W. G. and Rothman, J. E. *Cell* 42:13–21 (1985); Tarentino, A. L., et al. *J. Biol. Chem.* 249:818–824 (1974)). Thus the exit of Ab-sFv from the ER appears to be the rate limiting step in their secretion.

As a result of the work presented herein, soluble, secretable sFv molecules, including sFv fusion molecules, can be produced in mammalian cells. All secreted antibody sFv specifically bound the appropriate antigen, and where tested, at least 90% of the secreted sFv was functional. Therefore, mammalian cells can properly fold and secrete antibody sFv and the presence of oligosaccharide can enhance their rates of secretion. These sFv molecules are biologically active and readily isolated and purified from cell culture medium.

The sFv molecules produced by the method described herein are useful in any procedure where intact immunoglobulins (IgG), fragmented IgG, analogous Ig superfamily sFv analogues, or chimeric derivatives are used. An sFv antibody produced by the method described herein can be used in a diagnostic immunoassay procedure to detect the presence of a specific protein which is indicative of a disease condition. For example, an sFv antibody specific for a tumor marker found in blood or urine can be used in an ELISA to screen patients for a particular type of cancer. As another example, an sFv receptor protein can be used in an assay to screen peptides for biological activity which enhance or inhibit receptor activity. In particular, due to their smaller size, these sFv molecules are useful as in vivo targeting agents. For example, the sFv molecule can be used to deliver effector molecules such as cellular toxins to targeted cells or to deliver radioisotope to tumors (Huston, J. S., et al., *Intern Rev. Immurol.*, 10:195–219 (1993)).

The expression of sFv molecules in mammalian cells, as described herein, allows a rapid determination of the biological activity of a particular construct. This could be especially useful in the production and testing of fusion proteins, where both the sFv and its fusion partner must be correctly folded. In many such cases, it may prove impossible to fold such constructs in vitro, while the folding machinery in the ER of mammalian cells can produce active sFv fusion proteins in vivo. Additionally, the method described herein provides a rapid means of screening numerous sFv constructs, or provides the means to determine if a particular sFv construct encodes an active sFv protein (e.g., on a pilot scale). Once it has been determined that an active sFv protein is produced, other systems, such as stably transfected cell lines or transgenic animals or plants, can be used for large-scale production of the protein.

The present invention will now be illustrated by the following examples, which will further and more specifically illustrate the invention.

EXAMPLE 1 sFv Constructs

Constructs and primers used are shown in FIG. 1. All antibody sFv constructs contain a $V_L$-linker-$V_H$, L-chain leader sequences, and a C-terminal peptide tag (from the c-myc proto-oncogene). The TcR sFv construct contained a leader sequence to direct protein to the ER. The following primers were used to produce the constructs:

Primer 1, tgttaactgctcact TCT AGA ATG AGG ACC CCT GCT CAG TTT CTT GGA ATC TTG TTG CTC TGG TTT CCA GGT ATC AAA TGT GAC ATC AAG ATG ACC AGT CT. (SEQ ID NO: 1)

Primer 2, atata GAA TTC CTC GAG GAG CTC TTA TTA ATT CAG ATC CTC TTC TGA GAT GAG TTT TTG TTC TGA TAA AGC TTT TGA GGA GAC TGT. (SEQ ID NO: 2)

Primer 3, atata GAA TTC CTC GAG GAG CTC TTA TTA GAG TTC GTC CTT TTC GCT ATT CAG ATC CTC TTC TGA GAT GAG TTT TTG TTC TGA TAA AGC TTT TGA GGA GAC TGT. (SEQ ID NO: 3)

Primer 4, tgttaactgctcact TCT AGA ATG AGG ACC CCT GCT CAG TTT CTT GGA ATC TTG TTG CTC TGG TTT CCA GGT ATC AAA TGT GAC GTC GTC ATG ACC AGT CT CCA GCA. (SEQ ID NO: 4)

Primer 5, atata GGA TCC ATG AGG GCC CCT ACT GTC. (SEQ ID NO: 5)

Primer 6, atata GCG GCC GCC ACT CCC ACC TCC GCC AGA ACC TCC GCC TCC TGA TCC GCC ACC TCC TTT GAT TTC CAG CTT GGT GCC. (SEQ ID NO: 6)

Primer 7, atata GGC GGC CGC GAG GTG CAG CTG GTG GAG. (SEQ ID NO: 7)

Primer 8, atata CTC GAG TTA TTA ATT CAG ATC CTC TTC TGA GAT GAG TTT TTG TTC TGA TGA GGA GAC GGT GAC CAT GGT. (SEQ ID NO: 8)

Primer 9, atata TCT AGA GAG AAG ACA ACC AGC GAT TGG ACA GGG GCC ATG CAG AGG AAC CTG GGA GCT GTG CTG GGG ATT CTG TGG GTG CAG ATT TGC TGG GTG AGA GGA GAT CAG GTG GAG CAG AGT CCT TCA GCC. (SEQ ID NO: 9)

Primer 10, atata GGA TCC TCA CTA AGT CAC ATT TCT CAG ATC CTC. (SEQ ID NO: 10)

In all primers, underlined sequences indicate restriction sites, lower case letters designate nucleotides added to facilitate cutting with restriction enzymes, and bold letters designate added sequences encoding for amino acid residues not present in the template.

U7.6 and OKT9 AbsFv proteins and the 2B4 TcR-sFv constructs have been described in (Kurucz, I., et al. *Proc. Natl. Acad. Sci. U.S.A.* 90:3830–3834 (1993); Nicholls, P. J., et al. *J. Immunol. Methods* 165:81–91 (1993)). The nucleic acid sequence of U7.6 (SEQ ID NOs: 14 and 16) are shown in FIGS. 2A and 2B ($V_H$ region and $V_L$ region, respectively). Plasmids containing these constructs were used as polymerase chain reaction (PCR) templates. The OKT9 sFv construct was amplified using sense primer 1 that introduced an Xba I site and a light chain leader sequence and anti-sense primer 2 that introduced a c-myc peptide sequence, two stop codons, and a Sac I site. To construct the OKT9+KDEL (SEQ ID NO: 18) sFv sense primer 1 and an anti-sense primer 3 that is identical to primer 2 but adds an additional SEKDEL (SEQ ID NO: 19) sequence at the C terminal end were used. The PCR products were directly ligated into PCRIOO0 (Invitrogen, San Diego, Calif.), according to manufacturers instructions, and subcloned into the Xba I and Sac I site of pSVL (Pharmacia, Piscataway, N.J.). The U7.6 sFv construct was amplified using sense PCR-primer 4 that introduced an Xba I site and a light chain leader sequence followed by an Aat II site, and anti-sense primer 2.

Following the digestion of the purified PCR product with Xba I and Sac I the construct was directly ligated into the Xba I and Sac I site of pSVL. The 2C11 sFv was constructed from cDNA using primers based on the 2C11 V region sequences, kindly supplied by Dr. J. Yun Tso (Protein Design Labs, Mountain View, Calif.). Specifically primed first strand cDNA was synthesized from mRNA isolated from 2C11 cells (FASTRACK™ method from Invitrogen, San Diego, Calif.) by primer extension using reverse transcriptase (SUPERSCRIPT™ transcriptase Gibco/BRL, Grand Island, N.Y.). The light chain cDNA was synthesized using anti-sense primer 6 that introduces a $(G_4S)_3$ linker and a Not I site. This cDNA was used for amplification of $V_L$ using anti-sense primer 6 and sense primer 5, that introduces a BamH I site. The heavy chain cDNA was synthesized using anti-sense primer 8 that introduces a myc-peptide sequence and a Xho I site. This cDNA was used for amplification of the light chain using anti-sense primer 8 and sense primer 7 that introduces a Not I site at the 5' end. The PCR products were purified, blunted using T4 DNA polymerase (Boehringer Mannheim Indianapolis, Ind.) phosphorylated with T4 polynucleotide kinase (Gibco/BRL, Grand Island, N.Y.) and sub-cloned into pcDNA/AMP (Invitrogen, San Diego, Calif.) that had been cut with EcoR V and treated with calf alkaline phosphatase (Boehringer Mannheim). The light chain was excised with BamH I and Not I and the heavy chain with Not I and Xho I and both chains were simultaneously ligated into pcDNA/AMP digested with BamH I and Xho I.

Cloned 2B4 TcR-sFv (Kurucz, I., et al. *Proc. Natl. Acad. Sci. U.S.A.* 90:3830–3834 (1993)) was used as the PCR template for the TcR-sFv construct. The 2B4 sFv construct was amplified using sense primer 9 introducing an Xba I site (underlined), 30 bp of the α-chain 5'non-coding region and the α-chain leader sequence and anti-sense primer 10 that introduced a BamH I site. The PCR products were directly ligated into PCRIOO0 and subcloned into the Xba I and BamH I sites of pSVL.

Site directed mutagenesis of U7.6 Mutations in the U7.6 sFv constructs were introduced using a the TRANSFORMER-MUTAGENESIS™ mutagenesis protocal (Clonetech Laboratories Inc, Palo Alto, Calif.) according to the manufacturer's instructions except that ten times more plasmid was used than recommended. Colonies were screened using restriction enzyme digestion and plasmids from mutant clones were sequenced with a SEQUENASE VERSION 2.0™ sequencing method (United States Biochemical, Cleveland, Ohio). Constructs were recloned to eliminate possible changes introduced into the vector during mutagenesis. The primers used were: U7.6 –CYS, C TGC CAG CAG TaC AGT GGT TAC CCG, (SEQ ID NO: 11) introduced a tyrosine in place of cysteine 91 of $V_L$ (the original U7.6 $V_L$ clone contained a tyrosine residue at position 91; cysteine 91 was inadvertently introduced at a subsequent recloning step, probably as a PCR-induced mutation); U7.6+ASN, GGC GCT TCA GTG AAt ATA TCC TGC AAG GC, (SEQ ID NO: 12) introduced an asparagine for lysine 19 of $V_H$. As a selection primer we used CCC TTT CGT CTT CAA Gtt TTC TCA TGT TTG ACA GC (SEQ ID NO: 13) which removed an EcoR I site from the vector. In the above primers, lower case letters designate the mutated nucleotides. The double mutant, U7.6 –CYS+ASN, was produced by using all three primers simultaneously.

EXAMPLE 2
Transfection and Metabolic Labeling Cell Lines and Antibodies

The following cell lines and monoclonal antibodies were used: COS-7 monkey kidney fibroblasts and K562 human erythroleukemia cells (American Type Culture Collection, Rockville, Md.), 2B4 murine T hybridoma cells (Hedrick, S. M., et al., *Cell*, 30:141–152 (1982)), 145–2C11 hybridoma cells and mAb against murine CD3 ε chain (Leo, 0., et al., *Proc. Natl. Acad. Sci. USA* 84:1374–1378 (1987)), OKT9 mAb against human transferrin receptor (TfR) (Goding, J. W. and Burns, G. F. *J. Immunol.* 127:1256–1258 (1981); Schneider, C., et al., *J. Biol. Chem.* 257:8516–8522 (1982)), W6/32 mAb against human MHC Class I molecules (Barnstable, C. J., et al., *Cell*, 14:9–20 (1978)), H57 mAb against the $C_\beta$ domain of murine TcRs (Kubo, R. T., et al., *J. Immunol.*, 142:2736–2742 (1989)), 9EIO mAb against a c-myc peptide (Evan, G. I., et al., *Mol. Cell Biol.*, 5:3610–3616 (1985)), and A2B4 mAb, which is specific for the 2B4 TcR (Samelson, L. E., et al., *Proc. Natl. Acad. Sci. U.S.A.* 80:6972–6976 (1983)). Polyclonal rabbit anti-mouse IgG was from Cappel (Organon Technika, Durham, N.C.). COS-7 cells cultured in Dulbecco's modified Eagle's medium (DMEM) supplemented with penicillin (100 units/ml), streptomycin (100 units/ml), 2 mM L-glutamine, (all from Biofluids, Rockville, Md.), and 10% fetal calf serum (Hazelton Biochemicals, Lenexia, Kans.) were plated in 10-cm culture dishes. The next day the medium was changed and two hours later the cells were transfected with 20 μg of plasmid DNA [produced in *E. coli* strain HBIO1 (Gibco/BRL) and purified with a Qiagen (Chatsworth, Calif.) Plasmid Kit] using the calcium phosphate precipitation method (Davis, L. G., et al., *Basic methods in molecular biology*, Elsevier, N.Y. (1986)).

For pulse chase experiments COS-7 cells were trypsinized 16 h after transfection and replated in three 10-cm culture dishes to generate a uniform population of cells and minimize dish to dish variation. The cells were then allowed to grow for an additional 24 h. Cells in a 10-cm dish that were 90% confluent were preincubated for 20 min at 37° C. in methionine free-DMEM containing 10% fetal calf serum (dialyzed against PBS) after which [$^{35}$S]methionine (Trans$^{35}$S-label [ICN Radiochemicals, Irvine, Calif.]) was added to a concentration of 0.15 mCi/ml. The cells were pulsed for 1 h at 37° C. and then washed and chased in DMEM containing 15 mg/ml of L-methionine (chase medium)(Sigma Chemical Co., St. Louis, Mo.). Cells and culture media were collected separately. In some pulse-chase experiments cells were pretreated for 2 h, pulsed for 1 h, and chased for 2 h in medium that contained 3/μg/ml of tunicamycin (Sigma) throughout the experiment.

EXAMPLE 3
Isolation and Purification of Proteins Immunoprecipitation and endoglycosidase treatment Culture media were used immediately for immunoprecipitation. Cells were washed 3 times with cold PBS, scraped from the dishes and lysed overnight in 250 μl lysis buffer (50 mM Tris, 5 mM EDTA, 150 mM NaCI, 0.5% NP-40 (Calbiochem, San Diego, Calif.), 1 mM phenyl methyl sulfonyl fluoride (Sigma), pH 8.0). Nuclei were pelleted by centrifugation for 30 min at 12,000 g. Culture media (3 or 6 ml) or cell lysates (250 μl) were incubated for 3 h at 4° C. with gentle tumbling with 20 μl of packed Protein A-Sepharose beads (Pharmacia) precoated with rabbit IgG. The precleared samples were then centrifuged and incubated with 3 μg of either 9EIO or A2B4 mAb for 3 h, followed by 3–16 h incubation at 40° C. with 20–30 μl of packed Protein A-Sepharose precoated with rabbit anti-mouse Ig. The immunoprecipitates were washed three times with 5% sucrose, 1% NP40, 0.5M NaCI, 50 mM Tris, 5 mM EDTA, pH 7.2 and once with 50 mM Tris, 150 mM NaCI, 1% Triton X-100 (Sigma), 0.15% SDS, 1% sodium deoxycholate, and solubilized in 40 μl reducing SDS polyacrylamide gel electrophoresis (SDS-PAGE) sample buffer. Sequential immunoprecipitations using the same antibody were performed until less than 10% of the original protein remained in the supernatant. In some experiments immunoprecipitates were digested with endoglycosidase H (endo H) (Genzyme, Cambridge, Mass.), as described in (Kearse, K. P. and Singer, A., *J. Immunol. Methods* (1994)). Following endo H digestion, an equal volume of reducing SDS-PAGE sample buffer was added.

SDS-PAGE, autoradiography and densitometry

SDS-PAGE was performed using a Pharmacia PHAST-SYSTEM™ electrophoresis-system with 12.5% homogeneous PHASTGELS™ polyacrylamide gel. Samples were heated to 95° C. for 5 min, beads were removed by centrifugation and 3.5 μl aliquots of supernatant were applied to the gel. After electrophoresis, gels were incubated with shaking twice for 20 min in dimethyl sulfoxide, once for 2 h in 20% w/v 2,5-diphenyloxazole in dimethyl sulfoxide, and once for 30 min in $H_2O$. Gels were dried in a microwave oven for 20 min at the lowest power level and exposed to film (Kodak X-OMAT AR, Rochester, N.Y.) at --70° C. for 1–3 days. Autoradiograms were quantified with a Molecular Dynamics MOLECULAR DYNAMICS™ computing densitometer using IMAGEQUANT™ software. Exposure times were chosen to ensure linearity between radioactivity and band density. Multiple loadings of identical samples gave standard deviations in band densities of less than 10%.

EXAMPLE 4 sFv Binding Studies

Binding of sFv proteins was tested using the radiolabeled material present in the media of transfected COS-7 cells after either a 2 h or a 6 h chase. Binding of OKT9 and 2C11 sFv media was tested on K562 (TfR$^+$) and 2B4 (CD3$^+$) cells, respectively. Chase media containing (4 ml) 10 mM HEPES (Biofluids) were incubated for 4 hr at with 5–10×10$^6$ cells in 6 well plates, in the presence or absence of excess inhibiting or control antibodies. Inhibiting antibodies were the parental mAbs from which the sFv proteins were derived, and control antibodies were W6/32 and H57 for OKT9 and 2C11 respectively, both of which bind to the same cells as the sFv proteins, but to different antigens. After incubation and washing, cells were lysed in 250 µl lysis buffer, and sFv proteins were immunoprecipitated and analyzed by SDS-PAGE as described above. U7.6 sFv was tested for binding by incubation with gentle tumbling of 1.5 or 4 ml of chase medium with 50 µl of packed DNP-Sepharose beads for 16 h in the absence or presence of 1 mM DNP-ε-aminocaproate. The beads were washed and the bound sFv was solubilized in 40 µl reducing sample buffer in preparation for SDS-PAGE. In some studies, U7.6 sFv supernatants were incubated a second time with 50 µl of DNP-beads. The doubly-depleted supernatants were then assayed for residual sFv by immunoprecipitating with 9E 10 and rabbit anti-mouse protein A beads. Fractions were then analyzed using SDS-PAGE and the bands were quantified by densitometry.

In order to measure relative affinities of the U7.6 mutant sFv constructs, 1 ml aliquots of $^{35}$S-methionine labeled chase media containing 0.01 sodium azide, 10 mM HEPES, and graded amounts of DNP-ε-aminocaproate were incubated overnight at 4° C. with 40 µl of packed DNP-Sepharose beads. The beads were washed, and bound sFv removed by addition of 1 mM DNP-hapten for 6 hr at 4° C. The eluted sFv was immunoprecipitated with 9E10 mAb and protein A-Sepharose, and the beads were washed, divided into 4 equal portions, and heated for 5 min at 94° C. in 100 µl of elution buffer (20 mM Tris, 1 mM EDTA, 2% SDS and 5% 2ME pH 7.8). The eluate (85 µl) was transferred directly to 2.5 ml of ECOLUME™ scintillation solution (ICN Cleveland, Ohio) scintillation solution and counted in a liquid scintillation counter.

EXAMPLE 5

Dissociation of OKT9-sFv from K562 Cells

To measure the dissociation rate of COS-7 cell-produced OKT9-sFv from K562 cells, tubes containing 6×10$^6$ K562 or 2B4 (control) cells and 1 ml of COS-7 medium containing $^{35}$S-methionine labeled OKT9-sFv and supplemented with 0.01% sodium azide, 10 mM HEPES were incubated 1 h at 4° C. Cells were centrifuged for 5 min at 425×G. To determine the maximal amount of sFv bound (0 time), cells were resuspended in Hank's balanced salt solution without phenol red containing 0.1% BSA and 0.01% sodium azide (wash buffer), immediately spun for 10 sec in an EPPENDORF microcentrifuge, and the pellet frozen. Other samples were suspended in 1 ml wash buffer containing 50 µg OKT9 mAb, incubated for various times at 4° C., spun for 10 sec, and pellets frozen. Cell pellets were lysed and sFv immunoprecipitated with 9E10 mAb and protein A-Sepharose beads, and taken for scintillation counting as described above. Quadruplicate samples were averaged, and the amount of radioactivity associated with 2B4 cells was considered background and was subtracted from the amount binding to K562 cells.

The dissociation rate was also measured using bacterially-produced OKT9-sFv and flow cytometry. OKT9-sFv was produced and refolded from bacterial inclusion bodies, and labeled with fluorescein isothiocyante (FITC) as described in Segal, D. M. et al., *Meth. Enzymol.* 150:478–492 (1987) K562 cells (10$^7$) were incubated for 1 h at 4° C. with 2 µg OKT9-sFv-FITC, with or without 50 µg OKT9 mAb in a total volume of 1 ml. Cells were centrifuged for 5 min at 425×G, resuspended in 1 ml wash buffer containing 50 µg OKT9 mAb, and incubated at 4° C. At various times, samples were analyzed by flow cytometry. Mean fluorescence values were determined and control values (mean fluorescence of samples incubated with FITC-sFv in the presence of excess unlabeled mAb) were subtracted at each time point.

Equivalents

Those skilled in the art will recognize, or be able to ascertain, using no more than routine experimentation, many equivalents to the specific embodiments of the invention described herein. Such equivalents are intended to be encompassed by the following claims:

---

The invention claimed is:

1. A single-chain Fv antibody with antigen-binding activity comprising a light chain variable region ($V_L$, comprising SEQ ID NO: 17, and, heavy chain varible region ($V_H$, comprising a non-naturally occurring N-linked glycosylation site wherein an asparagine amino acid residue is substituted for lysine 19 of SEQ ID NO: 15.

2. A method of increasing the rate of secretion of a single-chain Fv antibody from mamnnalian cells, wherein the single-chain Fv antibody is modified to have a non-naturally occurring glycosyla-ion site and the antibody has antigen-binding activity, comprising the steps of:

(a) modifying a polynucleic acid which encodes a single-chain Fv antibody to include a non-naturally occurring N-linked glycosylation site in the first framework region of $V_H$ in the encoded amino acid sequence, thereby providing a single-chain Fv construct encoding a modified single-chain Fv artibody;

(b) introducing the single-chain Fv construct of step (a) into a vector which expresses said construct in a mammalian ceil and transfecting said vector containing the single-chain Fv construct into a competent mammalian cell; and (c) maintaining said cell transfected with the vector of step (b) in cell culture medium under conditions sufficient for expression of the single-chair Fv construct within the cell and secretion of the expressed modified single-chain Fv antibody from the cell into the cell culture medium, whereirn the modified single-chain Fv antibody is secreted into the cell culture medium at a faster rate than the unmodified single chain Fv antibody, and the modified single-chain Fv antibody has antigen-binding activity.

3. The method of claim 2 wnerein the non-naturally occurring glycosylation site is at position 19 of the $V_H$ framework region.

4. The method of claim 3 wherein the N-linked glycosylation site is Asn-X-Ser/Thr.

5. The method of claim 3 wherein the mammalian cell is selected from the group consisting of: cos-7 monkey kidney fibroblast cells; K562 human erythroleukemia cells; 293 cells; myeloma cells; and Chinese hamster ovary cells.

6. A method of producing a single-chain Fv antibody with antigen-binding activity and with an increased rate of secretion from mammalian cells, comprising the steps of:

(a) modifying a polynucleic acid sequence which encodes a single-chain Fv antibody to include a non-naturally occurring N-linked glycosylation site in the first framework region of $V_H$ in the encoded amino acid sequence, thereby providing a single-chain Fv construct encoding a modified single-chain Fv antibody;

(b) introducing the single-chain Fv construct of step (a) into a vector which expresses said construct in a mammalian cell and transfecting said vector containing the single-chain Fv construct into a competent mammalian cell; and (c) maintaining said cell transfected with the vector of step (b) in cell culture medium under conditions sufficient for expression of the single-chain Fv construct within the cell and secretion of the expressed modified single-chain Fv antibody from the cell into the cell culture medium, thereby producing a single-chain Fv antibody with antigen-binding activity and an increased rate of secretion from mammalian cells when compared with the rate of secretion of the unmodified single-chain Fv antibody.

7. A host cell transfected with a vector containing the single-chain Fv construct of claim 6.

8. A method of increasing the rate of secretion of a single-chain Fv antibody from mammalian cells comprising modifying the single-chain Fv antibody by introducing into the single-chain Fv antibody a non-naturally occurring N-linked glycosylation site in the first framework region of $V_H$, and secreting the modified single-chain Fv antibody from a mammalian cell, wherein the rate of secretion of the modified single-chain Fv antibody is increased as compared to the rate of secretion of the unmodified single-chain Fv antibody, and the modified single-chain Fv antibody retains its antigen-binding activity.

9. The method of claim 8 wherein the glycosylation site is an N-linked glycosylation site at position 19 of $V_H$.

10. The method of claim 9 wherein the glycosylation site is Asn-x-Ser/Thr.

11. A method of producing, in mammalian cells, a single-chain Fv antibody with antigen-binding activity comprising a $V_L$ comprising SEQ ID NO: 17 and a $V_H$ comprising a non-naturally occurring N-linked gycosylation site, comprising the steps of:

(a) modifying a polynucleic acid which encodes the single-chain Fv antibody comprising SEQ ID NO: 17 to include a non-naturally occurring N-linked glycosylation site in the $V_H$, wherein the glycosylation site comprises an asparagine amino acid residue substituted for lysine 19 of SEQ ID NO: 15, thereby providing a single-chain Fv construct;

(b) introducing the single-chain Fv construct of step (a) into a vector which expresses said construct in a mammalian cell and transfecting said vector containing the single-chain Fv construct into a competent mammalian cell; and (c) maintaining said cell transfected with the vector of step (b) in cell culture medium under conditions sufficient for expression of the single-chain Fv construct within the cell and secretion of the expressed single-chain Fv antibody from the cell into cell culture medium, thereby producing a single-chain Fv antibody with antigen-binding activity and a non-naturally occurring glycosylation site in the $V_H$.

12. The method of claim 11 wherein the polynucleic acid encoding the single-chain Fv antibody comprises SEQ ID NO: 16 and SEQ ID NO: 14, wherein a codon for asparagine is substituted for the codon for lysine at position 19 of SEQ ID NO: 14.

13. A host cell transfected with a vector containing the single-chain Fv construct of claim 11.

14. A single-chain Fv antibody produced by the method of claim 11.

* * * * *

UNITED STATES PATENT AND TRADEMARK OFFICE
CERTIFICATE OF CORRECTION

PATENT NO. : 5,888,773
DATED : Mar. 30, 1999
INVENTOR(S) : Carolina R. Jost, et al It is certified that error appears in the above-identified patent and that said Letters Patent is hereby corrected as shown below:

On the title page, item [75], Inventor(s): should read

Carolina R. Jost, Washington, D.C.; David M. Segal, Rockville, Md

Signed and Sealed this

Twenty-third Day of May, 2000

Attest:

Q. TODD DICKINSON

*Attesting Officer*  *Director of Patents and Trademarks*

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 102 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:1:

```
TGTTAACTGC   TCACTTCTAG   AATGAGGACC   CCTGCTCAGT   TTCTTGGAAT   CTTGTTGCTC         60

TGGTTTCCAG   GTATCAAATG   TGACATCAAG   ATGACCCAGT   CT                            102
```

( 2 ) INFORMATION FOR SEQ ID NO:2:

( i ) SEQUENCE CHARACTERISTICS:
    ( A ) LENGTH: 86 base pairs
    ( B ) TYPE: nucleic acid
    ( C ) STRANDEDNESS: single
    ( D ) TOPOLOGY: linear ( i i ) MOLECULE TYPE:

( x i ) SEQUENCE DESCRIPTION: SEQ ID NO:2:

```
ATATAGAATT CCTCGAGGAG CTCTTATTAA TTCAGATCCT CTTCTGAGAT GAGTTTTGT      60
TCTGATAAAG CTTTTGAGGA GACTGT                                          86
```

( 2 ) INFORMATION FOR SEQ ID NO:3:

( i ) SEQUENCE CHARACTERISTICS:
    ( A ) LENGTH: 104 base pairs
    ( B ) TYPE: nucleic acid
    ( C ) STRANDEDNESS: single
    ( D ) TOPOLOGY: linear ( i i ) MOLECULE TYPE:

( x i ) SEQUENCE DESCRIPTION: SEQ ID NO:3:

```
ATATAGAATT CCTCGAGGAG CTCTTATTAG AGTTCGTCCT TTTCGCTATT CAGATCCTCT     60
TCTGAGATGA GTTTTTGTTC TGATAAAGCT TTTGAGGAGA CTGT                     104
```

( 2 ) INFORMATION FOR SEQ ID NO:4:

( i ) SEQUENCE CHARACTERISTICS:
    ( A ) LENGTH: 108 base pairs
    ( B ) TYPE: nucleic acid
    ( C ) STRANDEDNESS: single
    ( D ) TOPOLOGY: linear ( i i ) MOLECULE TYPE:

( x i ) SEQUENCE DESCRIPTION: SEQ ID NO:4:

```
TGTTAACTGC TCACTTCTAG AATGAGGACC CCTGCTCAGT TTCTTGGAAT CTTGTTGCTC      60
TGGTTTCCAG GTATCAAATG TGACGTCGTC ATGACCAGT CTCCAGCA                  108
```

( 2 ) INFORMATION FOR SEQ ID NO:5:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE:

( x i ) SEQUENCE DESCRIPTION: SEQ ID NO:5:

```
ATATAGGATC CATGAGGGCC CCTACTGTC                                       29
```

( 2 ) INFORMATION FOR SEQ ID NO:6:

( i ) SEQUENCE CHARACTERISTICS:
    ( A ) LENGTH: 80 base pairs
    ( B ) TYPE: nucleic acid
    ( C ) STRANDEDNESS: single
    ( D ) TOPOLOGY: linear ( i i ) MOLECULE TYPE:

( x i ) SEQUENCE DESCRIPTION: SEQ ID NO:6:

```
ATATAGCGGC CGCCACTCCC ACCTCCGCCA GAACCTCCGC CTCCTGATCC GCCACCTCCT      60
```

TTGATTTCCA GCTTGGTGCC                                                                    80

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:7:

ATATAGGCGG CCGCGAGGTG CAGCTGGTGG AG                                                       32

(2) INFORMATION FOR SEQ ID NO:8:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:8:

ATATACTCGA GTTATTAATT CAGATCCTCT TCTGAGATGA GTTTTGTTC TGATGAGGAG                          60

ACGGTGACCA TGGT                                                                          74

(2) INFORMATION FOR SEQ ID NO:9:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:9:

ATATATCTAG AGAGAAGACA ACCAGCGATT GGACAGGGGC CATGCAGAGG AACCTGGGAG                         60

CTGTGCTGGG GATTCTGTGG GTGCAGATTT GCTGGGTGAG AGGAGATCAG GTGGAGCAGA                        120

GTCCTTCAGC C                                                                            131

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:10:

ATATAGGATC CTCACTAAGT CACATTTCTC AGATCCTC                                                 38

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE:

(xi) SEQUENCE DESCRIPTION: SEQ ID NO:11:

CTGCCAGCAG TACAGTGGTT ACCCG 25

( 2 ) INFORMATION FOR SEQ ID NO:12:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:12:

GGCGCTTCAG TGAATATATC CTGCAAGGC 29

( 2 ) INFORMATION FOR SEQ ID NO:13:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE:

( x i ) SEQUENCE DESCRIPTION: SEQ ID NO:13:

CCCTTTCGTC TTCAAGTTTT CTCATGTTTG ACAGC 35

( 2 ) INFORMATION FOR SEQ ID NO:14:

( i ) SEQUENCE CHARACTERISTICS:
        ( A ) LENGTH: 360 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..360

( x i ) SEQUENCE DESCRIPTION: SEQ ID NO:14:

```
CAG  GTC  CAA  CTG  CAG  CAG  TCT  GGA  CCT  GAG  CTG  GAG  AAG  CCT  GGC  GCT     48
Gln  Val  Gln  Leu  Gln  Gln  Ser  Gly  Pro  Glu  Leu  Glu  Lys  Pro  Gly  Ala
 1                   5                        10                       15

TCA  GTG  AAG  ATA  TCC  TGC  AAG  GCT  TCT  GGT  TAC  TCA  TTC  ACT  GGC  TAC     96
Ser  Val  Lys  Ile  Ser  Cys  Lys  Ala  Ser  Gly  Tyr  Ser  Phe  Thr  Gly  Tyr
                    20                       25                       30

ATC  ATG  AAC  TGG  GTA  AAA  CAG  AAC  AAT  GGA  AAG  AGC  CTT  GAG  TGG  ATT    144
Ile  Met  Asn  Trp  Val  Lys  Gln  Asn  Asn  Gly  Lys  Ser  Leu  Glu  Trp  Ile
               35                        40                       45

GGA  AAT  ATT  GCT  CCT  TAC  TAT  GGT  GGT  ACT  AGC  TAC  AAC  CAG  AAG  TTC    192
Gly  Asn  Ile  Ala  Pro  Tyr  Tyr  Gly  Gly  Thr  Ser  Tyr  Asn  Gln  Lys  Phe
      50                       55                       60

AAG  GGC  AAG  GCC  ACA  TTG  ACT  GTA  GAC  AAA  TCC  TCC  AGC  ACA  GCC  TAC    240
Lys  Gly  Lys  Ala  Thr  Leu  Thr  Val  Asp  Lys  Ser  Ser  Ser  Thr  Ala  Tyr
 65                       70                       75                       80

ATG  CAG  CTA  AGC  AGC  CTG  ACA  TCT  GAG  GAC  TCT  GCA  GTC  TAT  TTC  TGT    288
Met  Gln  Leu  Ser  Ser  Leu  Thr  Ser  Glu  Asp  Ser  Ala  Val  Tyr  Phe  Cys
                    85                       90                       95

GCA  AGA  TGG  GGA  GGT  ACT  ATG  ATT  ACG  GGT  CTT  GAC  TAC  TGG  GGC  CAA    336
Ala  Arg  Trp  Gly  Gly  Thr  Met  Ile  Thr  Gly  Leu  Asp  Tyr  Trp  Gly  Gln
                   100                      105                     110

GGC  ACC  ACT  CTC  ACA  GTC  TCC  TCA                                             360
Gly  Thr  Thr  Leu  Thr  Val  Ser  Ser
```

115 120

(2) INFORMATION FOR SEQ ID NO:15:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO:15:

```
Gln Val Gln Leu Gln Gln Ser Gly Pro Glu Leu Glu Lys Pro Gly Ala
 1               5                  10                  15
Ser Val Lys Ile Ser Cys Lys Ala Ser Gly Tyr Ser Phe Thr Gly Tyr
            20                  25                  30
Ile Met Asn Trp Val Lys Gln Asn Gly Lys Ser Leu Glu Trp Ile
        35                  40                  45
Gly Asn Ile Ala Pro Tyr Tyr Gly Gly Thr Ser Tyr Asn Gln Lys Phe
     50                  55                  60
Lys Gly Lys Ala Thr Leu Thr Val Asp Lys Ser Ser Ser Thr Ala Tyr
 65                  70                  75                  80
Met Gln Leu Ser Ser Leu Thr Ser Glu Asp Ser Ala Val Tyr Phe Cys
                85                  90                  95
Ala Arg Trp Gly Gly Thr Met Ile Thr Gly Leu Asp Tyr Trp Gly Gln
               100                 105                 110
Gly Thr Thr Leu Thr Val Ser Ser
               115                 120
```

(2) INFORMATION FOR SEQ ID NO:16:

(i) SEQUENCE CHARACTERISTICS:
        (A) LENGTH: 327 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..327

(xi) SEQUENCE DESCRIPTION: SEQ ID NO:16:

```
GAT ATT GTC ATG ACC CAG TCT CCA GCA ATC ATG TCT GCA TCT CCA GGG    48
Asp Ile Val Met Thr Gln Ser Pro Ala Ile Met Ser Ala Ser Pro Gly
             125                 130                 135
GAA AAG GTC ACC ATG ACC TGC AGG GCC AGC TCA AGT GTA AGT TCC ACT    96
Glu Lys Val Thr Met Thr Cys Arg Ala Ser Ser Ser Val Ser Ser Thr
         140                 145                 150
TAC TTC CAC TGG TAC CAG CAG AAG TCA GGT GCC TCC CCC AAA CTC TGG   144
Tyr Phe His Trp Tyr Gln Gln Lys Ser Gly Ala Ser Pro Lys Leu Trp
             155                 160                 165
ATT TAT AGC ACA TCC ACC TTG GCT TCT GGA GTC CCT GCT CGC TTC AGT   192
Ile Tyr Ser Thr Ser Thr Leu Ala Ser Gly Val Pro Ala Arg Phe Ser
         170                 175                 180
GGC AGT GGG TCT GGG ACC TCT TAC TCT CTC ACA ATC AGC AGT GTG GAG   240
Gly Ser Gly Ser Gly Thr Ser Tyr Ser Leu Thr Ile Ser Ser Val Glu
185                 190                 195                 200
GCT GAA GAT GCT GCC ACT TAT TAC TGC CAG CAG TAC AGT GGT TAC CCG   288
Ala Glu Asp Ala Ala Thr Tyr Tyr Cys Gln Gln Tyr Ser Gly Tyr Pro
             205                 210                 215
CTC ACG TTC GGT GCT GGG ACC AAG CTG GAG CTG AAA CGC                327
```

```
Leu  Thr  Phe  Gly  Ala  Gly  Thr  Lys  Leu  Glu  Leu  Lys  Arg
               220                 225
```

(2) INFORMATION FOR SEQ ID NO:17:

(i) SEQUENCE CHARACTERISTICS:
        (A) LENGTH: 109 amino acids
        (B) TYPE: amino acid
        (D) TOPOLOGY: linear (ii) MOLECULE TYPE: protein (xi) SEQUENCE DESCRIPTION: SEQ ID NO:17:

```
Asp  Ile  Val  Met  Thr  Gln  Ser  Pro  Ala  Ile  Met  Ser  Ala  Ser  Pro  Gly
 1                   5                        10                       15
Glu  Lys  Val  Thr  Met  Thr  Cys  Arg  Ala  Ser  Ser  Ser  Val  Ser  Ser  Thr
               20                      25                       30
Tyr  Phe  His  Trp  Tyr  Gln  Gln  Lys  Ser  Gly  Ala  Ser  Pro  Lys  Leu  Trp
          35                      40                       45
Ile  Tyr  Ser  Thr  Ser  Thr  Leu  Ala  Ser  Gly  Val  Pro  Ala  Arg  Phe  Ser
     50                       55                      60
Gly  Ser  Gly  Ser  Gly  Thr  Ser  Tyr  Ser  Leu  Thr  Ile  Ser  Ser  Val  Glu
 65                      70                      75                        80
Ala  Glu  Asp  Ala  Ala  Thr  Tyr  Tyr  Cys  Gln  Gln  Tyr  Ser  Gly  Tyr  Pro
                    85                      90                       95
Leu  Thr  Phe  Gly  Ala  Gly  Thr  Lys  Leu  Glu  Leu  Lys  Arg
               100                 105
```

(2) INFORMATION FOR SEQ ID NO:18:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:18:

```
Lys  Asp  Glu  Leu
 1
```

(2) INFORMATION FOR SEQ ID NO:19:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:19:

```
Ser  Glu  Lys  Asp  Glu  Leu
 1                    5
```